United States Patent
Korovina et al.

(10) Patent No.: US 10,988,570 B2
(45) Date of Patent: Apr. 27, 2021

(54) MOLECULES AND OLIGOMERS FOR ENDOTHERMIC SINGLET FISSION

(71) Applicant: Alliance for Sustainable Energy, LLC, Golden, CO (US)

(72) Inventors: Nadezhda Korovina, Boulder, CO (US); Justin Carter Johnson, Denver, CO (US); Christopher Harry Chang, Golden, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 16/840,636

(22) Filed: Apr. 6, 2020

(65) Prior Publication Data
US 2020/0317855 A1 Oct. 8, 2020

Related U.S. Application Data

(60) Provisional application No. 62/829,743, filed on Apr. 5, 2019, provisional application No. 62/915,285, filed on Oct. 15, 2019.

(51) Int. Cl.
| | | |
|---|---|---|
| C07C 43/215 | (2006.01) | |
| C07C 41/01 | (2006.01) | |
| C08G 61/02 | (2006.01) | |

(52) U.S. Cl.
CPC ............ C08G 61/02 (2013.01); C07C 43/215 (2013.01); C07C 41/01 (2013.01);
(Continued)

(58) Field of Classification Search
None
See application file for complete search history.

(56) References Cited

U.S. PATENT DOCUMENTS

2007/0107835 A1 * 5/2007 Roberts ............... H01L 51/007
156/230

FOREIGN PATENT DOCUMENTS

WO WO-2017167633 A1 * 10/2017 ....... G01N 33/54346

OTHER PUBLICATIONS

Hayashi, K. et al. "Observation of Circularly Polarized Luminescence of the Excimer from Two Perylene Cores in the Form of [4] Rotaxane" Chem. Eur. J. 2018, 24, 14613-14616 (Year: 2018).*
(Continued)

*Primary Examiner* — Medhanit W Bahta
(74) *Attorney, Agent, or Firm* — Michael A. McIntyre

(57) ABSTRACT

The present disclosure relates to a composition that includes a repeat unit defined by

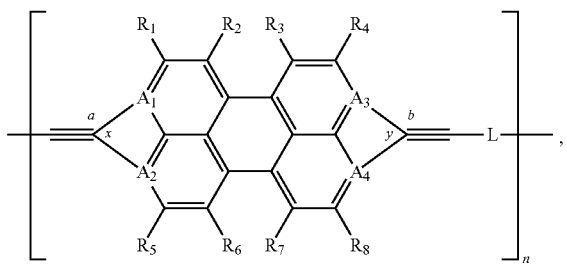

where each of $R_1$, $R_2$, $R_3$, $R_4$, $R_5$, $R_6$, $R_7$, and $R_8$ includes at least one of a hydrogen atom, a fluorine atom, and/or a first hydrocarbon chain having between 1 and 20 carbon atoms, inclusively, where each of $A_1$, $A_2$, $A_3$ and $A_4$ are either a carbon atom or a nitrogen atom, when $A_1$ is a nitrogen atom, $A_2$ is a carbon atom, when $A_2$ is a nitrogen atom, $A_1$ is a carbon atom, when $A_3$ is a nitrogen atom, $A_4$ is a carbon
(Continued)

atom, when $A_4$ is a nitrogen atom, $A_3$ is a carbon atom, either $A_1$ or $A_2$ form a covalent bond, x, with a carbon atom, a, either $A_3$ or $A_4$ form a covalent bond, y, with a carbon atom, b, L is a linker group that includes an aromatic ring, and n is between 1 and 20, inclusively.

7 Claims, 22 Drawing Sheets

(52) U.S. Cl.
CPC .. *C07C 2603/52* (2017.05); *C08G 2261/1412* (2013.01); *C08G 2261/1424* (2013.01); *C08G 2261/1646* (2013.01); *C08G 2261/226* (2013.01); *C08G 2261/312* (2013.01); *C08G 2261/314* (2013.01); *C08G 2261/3328* (2013.01); *C08G 2261/415* (2013.01); *C08G 2261/72* (2013.01)

(56) References Cited

OTHER PUBLICATIONS

Albrecht, W.G. et al., Exciton Fission in Excimer Forming Crystal Dynamics of an Excimer Build-up in α-Perylene, Chemical Physics, vol. 35, 1978, 8 pages.
Arias, D. et al., "Thermally-Limited Exciton Delocalization in Superradiant Molecular Aggregates," Journal of Phys. Chem. B, vol. 117, 2013, 7 pages.
Basel, B. et al., "Unified model for singlet fission within a non-conjugated covalent pentacene dimer," Nature Communications, DOI: 10.1038/ncomms15171, 8 pages.
Breen, I. et al., "Triplet Separation Drives Singlet Fission after Femtosecond Correlated Triplet Pair Production in Rubrene," Journal of the American Chemical Society, vol. 139, 2017, 7 pages.
Broch, K. et al., "Robust singlet fission in pentacene thin films with tuned charge transfer interactions," Nature Communications, 2018, DOI:10.1038/s41467-018-03300-1; 9 pages.
Chen, M. et al., "Quintet-triplet mixing determines the fate of the multiexciton state produced by singlet fission in a terrylenediimide dimer at room temperature," PNAS, vol. 116, No. 17, Apr. 23, 2019, 6 pages.
Congreve, D. et al., "External Quantum Efficiency Above 100% in a Single-Exciton-Fission-Based Organic Photovoltaic Cell," Science, vol. 340, Apr. 19, 2013, 5 pages.
Contoret, A. et al., "Electroluminescent Liquid Crystals," Mol. Cryst. and Liq. Cryst., vol. 368, 2001, 8 pages.
Dykstra, T. et al., "Conformational Disorder and Ultrafast Exciton Relaxation in PPV-family Conjugated Polymers," Journal of Phys,. Chem. B, vol. 113, 2009, 12 pages.
Eastwood, A.J. et al., "Synthesis and luminous properties of electroluminescent liquid crystals," Elsevier Synthetic Metals, vol. 121, 2001, 2 pages.
Fujitsuka, M. et al., "Size-dependent fluorescence properties of [n]cycloparaphenylenes (n=8-13), hoop-shaped u-conjugated molecules," Phys. Chem. Chem. Phys, vol. 14, 2012, 4 pages.
Gu, J. et al., "Valence Bond Theory Reveals Hidden Delocalized Diradical Character of Polyenes," Journal of the American Chemical Society, vol. 139, 2017, 15 pages.
Gupta, R.K. et al., "Perylene-Based Liquid Crystals as Materials for Organic Electronics Applications," Langmuir, 2018, DOI:10.1021/acs.langmuir.8b01081; 25 pages.
Hanna, M. et al., "Solar conversion efficiency of photovoltaic and photoelectrolysis cells with carrier multiplication absorbers," Journal of Applied Physics, vol. 100, 2006, 8 pages.

Hayashi, K. et al., "Reliable and Reproducible Separation of 3,9- and 3,10-Dibromoperylenes and the Photophysical Properties of Their Alkynyl Derivatives," European Journal of Organic Chemistry, 2017, 4 pages.
Ji, E et al., "Antibacterial Activity of Conjugated Polyelectrolytes with Variable Chain Lengths," Langmuir, vol. 27, 2011, 7 pages.
Johnson, J. et al., "Toward Designed Singlet Fission: Solution Photophysics of Two Indirectly Coupled Covalent Dimers of 1,3-Diphenylisobensofuran," Journal of Phys. Chem. B, vol. 117, 2013, 16 pages.
Korovina, N. et al., "Singlet Fission in a Covalently Linked Cofacial Alkynyltetracene Dimer," Journal of the American Chemical Society, vol. 138, 2016, 11 pages.
Korovina, N. et al., "Linker-Dependent Singlet Fission in Tetracene Dimers," Journal of the American Chemical Society, vol. 140, 2018, 12 pages.
Markiewicz, J. et al, "Perylene, Oligorylenes, and Aza-Analogs," Applied Materials and Interfaces, vol. 7, 2015, 23 pages.
Micozzi, A. et al., "Use of the Pd-Promoted Extended One-Pot (EOP) Synthetic Protocol for the Modular construction of Poly-(arylene ethynylene) co-Polymers [-Ar-C≡C-Ar'-C≡C-]n, Opto- and Electro-Responsive Materials for Advanced Technology," Adv. Synth. CataL, vol. 347, 2005, 18 pages.
Minami, T. et al., "Theoretical Study of Singlet Fission in Oligorylenes," Journal of Physical Chemistry Letters, vol. 3, 2012, 5 pages.
Pace, N. et al., "Controlling Long-Lived Triplet Generation from Intramolecular Singlet Fission in the Solid State," Journal of Phys. Chem. Letters, vol. 8, 2017, 6 pages.
Park, K. H. et al., "Excited-state structural relaxation and exciton delocalization dynamics in linear and cyclic rr-conjugated oligothiophense," Chem. Soc. Review, vol. 47, 2018, 6 pages.
Peeks, M. et al., "Experimental and computational evaluation of the barrier to torsional rotation in a butadiyne-linked porphyrin dimer," Phys. Chem. Chem. Phys., vol. 18, 2016, 11 pages.
Pensack, R. et al., "Observation of Two Triplet-Pair Intermediates in Singlet Exciton Fission," Journal of Phys. Chem. Letters, vol. 7, 2016, 6 pages.
Pensack, R. et aL, "The Nature of Excimer Formation in Crystalline Pyrene Nanoparticles," Journal of Phys. Chem. C, vol. 122, 2018, 14 pages.
Schrauben, J. et al., "Photocurrent Enhanced by Singlet Fission in a Dye-Sensitized Solar Cell," Applied Materials & Interfaces, vol. 7, 2015, 8 pages.
Schutze, F. et al., "Size Control of Spherical and Anisotropic Fluorescent Polymer Nanoparticles via Precise Rigid Molecules," Macromolecules, vol. 48, 2015, 7 pages.
Sharma, S. et al., "Naphthalene Diimide Copolymers by Direct Arylation Polycondensation as Highly Table Supercapacitor Electrode Materials, " Macromolecules, vol. 51, 2018, 12 pages.
Stern, Fl et al., "Identification of a triplet pair intermediate in singlet exciton fission in solution," PNAS, vol. 112, No. 25, Jun. 23, 2015, 6 pages.
Winters, M. et al., "Photophysics of a Butadiyne-Linked Porphyrin Dimer: Influence of Conformational Flexibility in the Ground and First Singlet Excited State," Journal of Phys. Chem. C, vol. 111, 2007, 8 pages.
Wong, K.S. et al., "Ultrafast excited-state planarization of the hexamethylsexithiophene oligomer studied by bmtosecond time-resolved photoluminescence," Chemical Physics Letters, vol. 288, 1998, 6 pages.
Umeyama, T. et al., "Synthesis and Photophysical and Photovoltaic Properties of Porphyrin-Furan and Thiophene Alternating Copolymers," Journal of Phys. Chem. C, vol. 113, 2009, 9 pages.
Zhao, X. et al., "Polymer Chain Length Dependence of Amplified Fluorescence Quenching in Conjugated Polyelectrolytes," Macromolecules, vol. 41, 2008, 7 pages.
Pace, N. et al., "Dynamics of singlet fission and electron injection in self-assembled acene monolayers on titanium lioxide," Chemical Science, vol. 9, 2018, 10 pages.

* cited by examiner

MOLECULES AND OLIGOMERS FOR ENDOTHERMIC SINGLET FISSION

CROSS-REFERENCE TO RELATED APPLICATIONS

This application claims priority from U.S. Provisional Patent Application Nos. 62/829,743 and 62/915,285 filed Apr. 5, 2019 and Oct. 15, 2019, respectively, the disclosures of which are incorporated herein by reference in their entirety.

CONTRACTUAL ORIGIN

This invention was made with government support under Contract No. DE-AC36-08GO28308 awarded by the Department of Energy. The government has certain rights in the invention.

SUMMARY

An aspect of the present disclosure is a composition that includes a repeat unit defined by

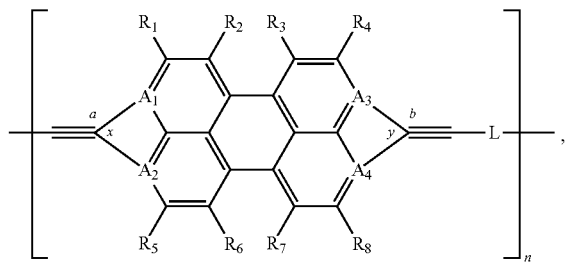

where each of $R_1$, $R_2$, $R_3$, $R_4$, $R_5$, $R_6$, $R_7$, and $R_8$ includes at least one of a hydrogen atom, a fluorine atom, and/or a first hydrocarbon chain having between 1 and 20 carbon atoms, inclusively, where each of $A_1$, $A_2$, $A_3$ and $A_4$ are either a carbon atom or a nitrogen atom, when $A_1$ is a nitrogen atom, $A_2$ is a carbon atom, when $A_2$ is a nitrogen atom, $A_1$ is a carbon atom, when $A_3$ is a nitrogen atom, $A_4$ is a carbon atom, when $A_4$ is a nitrogen atom, $A_3$ is a carbon atom, either $A_1$ or $A_2$ form a covalent bond, x, with a carbon atom, a, either $A_3$ or $A_4$ form a covalent bond, y, with a carbon atom, b, L is a linker group that includes an aromatic ring, and n is between 1 and 20, inclusively.

In some embodiments of the present disclosure, L may include at least one of

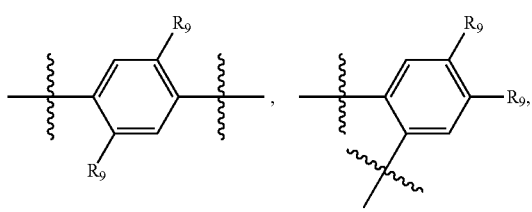

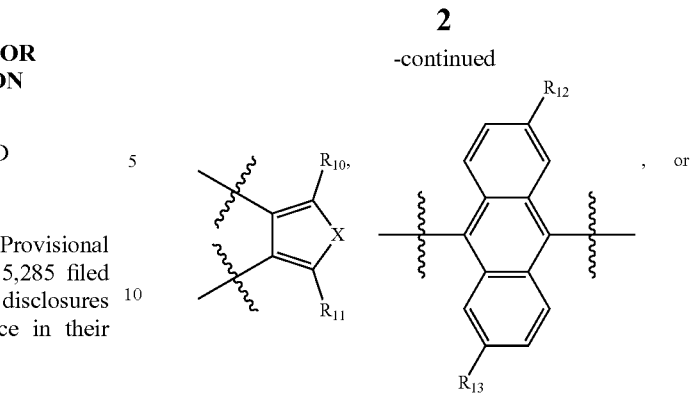

where $R_9$ may include a second hydrocarbon chain end-capped with at least one of an amine functional group, a carboxylic acid functional group, and/or a hydroxyl group, the second hydrocarbon chain may include between 1 and 20 carbon atoms, inclusively, each of $R_{10}$ and $R_{11}$ may include at least one of a hydrogen atom, a methyl group, and/or a methyl group end-capped with a hydroxyl group, each of $R_{12}$ and $R_{13}$ may include at least one of a hydrogen atom, a tert-butyl group, or a benzene ring, and each of $R_{14}$ and $R_{15}$ may include at least one of a hydrogen atom and/or a functional group constructed of a third hydrocarbon chain having an oxygen atom.

In some embodiments of the present disclosure, the composition may further include a terminal group that may include at least one of

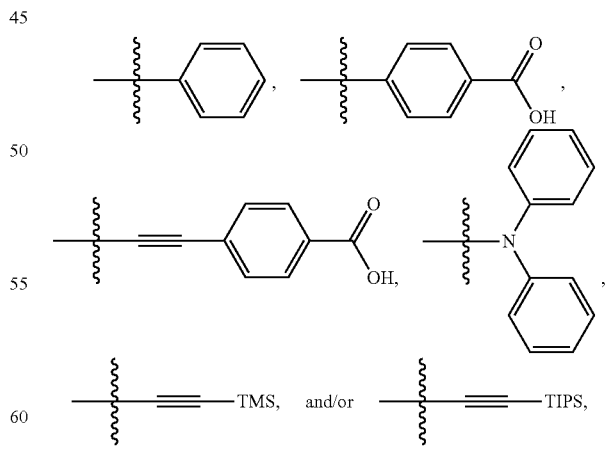

where TMS and TIPS are trimethylsilyl and triisopropylsilyl, respectively.

In some embodiments of the present disclosure, the repeat unit may be defined by

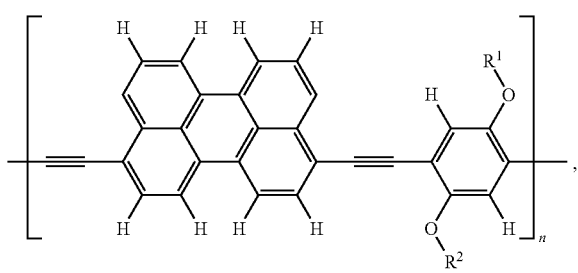

where $R^1$ and $R^2$ each may include a hydrocarbon chain having between 1 and 10 carbon atoms, and n may be between 1 and 10, inclusive.

In some embodiments of the present disclosure, $R^1$ and $R^2$ may each include

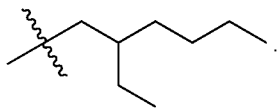

In some embodiments of the present disclosure, n may be between 2 and 4, inclusive. In some embodiments of the present disclosure, the composition may further include a triplet value of about 1.25 eV. In some embodiments of the present disclosure, the composition may further include a $\lambda_{max}$ value between about 538 nm and about 550 nm. In some embodiments of the present disclosure, the composition may further include a stimulated emission between about 550 nm and about 620 nm. In some embodiments of the present disclosure, the composition may further include a $E(S_1)$ value between about 2.21 eV and about 2.27 eV.

BACKGROUND

Organic chromophores undergoing singlet fission (SF), wherein a photoexcited singlet exciton splits into a pair of triplet excitons, have garnered attention in the last decade as promising active materials in optoelectronic devices, having the potential to raise power conversion efficiencies of photovoltaic devices beyond the Shockley-Queisser limit of 40%. However, strategic material design is essential for advancement of these compounds toward applications. Thus, there remains a need for improved chromophores.

BRIEF DESCRIPTION OF THE DRAWINGS

Some embodiments are illustrated in referenced figures of the drawings. It is intended that the embodiments and figures disclosed herein are to be considered illustrative rather than limiting.

FIG. 10A illustrates 2-OPP data, FIG. 10B illustrates 3-OPP data, and FIG. 10C illustrates 4-OPP data.

DETAILED DESCRIPTION

Figure 1A:
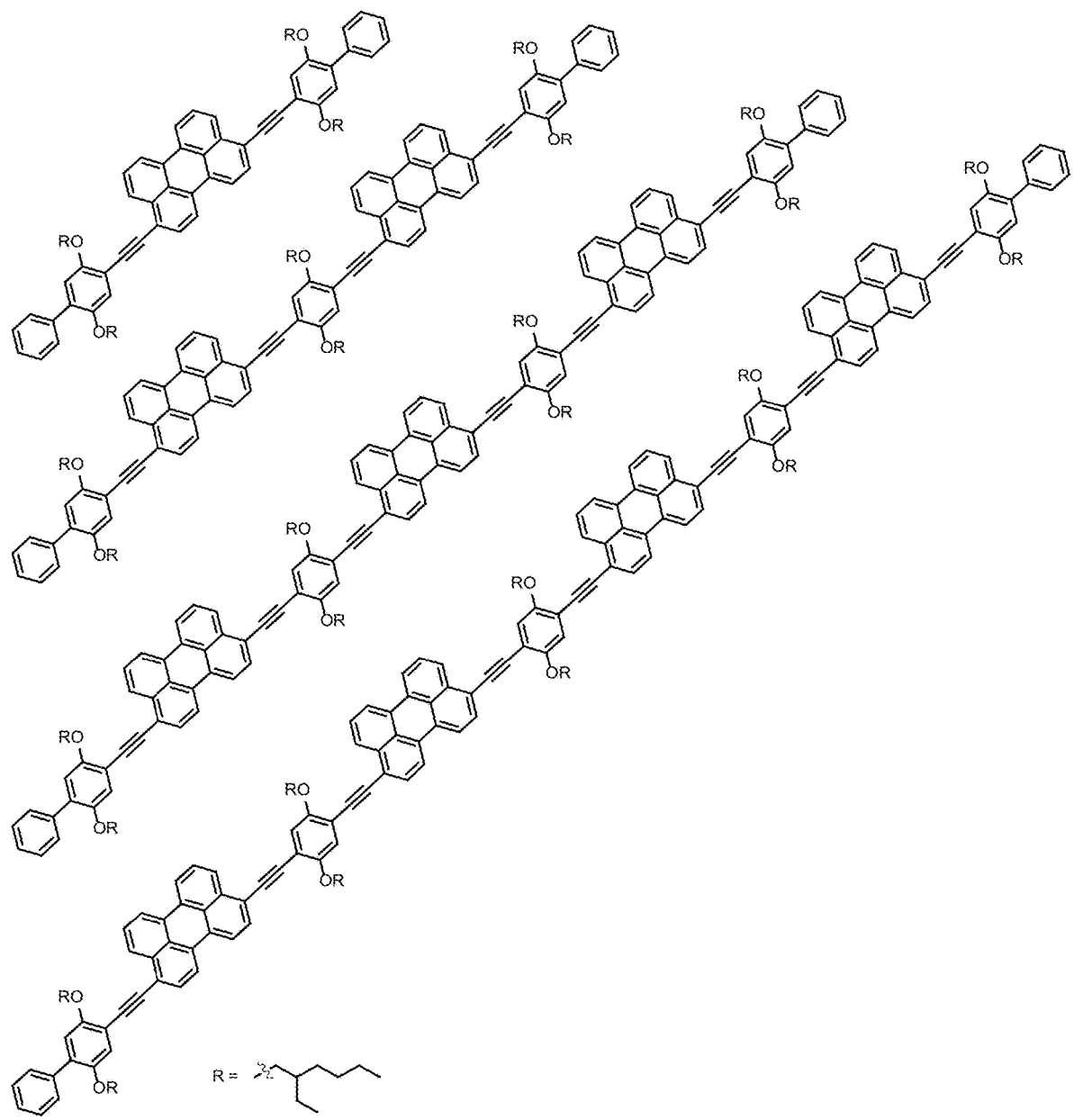
FIG. 1A illustrates exemplary chemical structures of oligomers derived from perylene, referred to hereinafter, from top to bottom 1-OPP, 2-OPP, 3-OPP, and 4-OPP, according to some embodiments of the present disclosure.

The present disclosure may address one or more of the problems and deficiencies of the prior art discussed above. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to 20%, 15%, 10%, +5%, or 1% of a specific numeric value or target. In some embodiments of the present invention, the term "about" is used to indicate an uncertainty limit of less than or equal to 1%, ±0.9%, 0.8%, ±0.7%, ±0.6%, 0.5%, ±0.4%, ±0.3%, ±0.2%, or 0.1% of a specific numeric value or target.

It is shown herein that significantly endothermic singlet fission can be activated through cooperation of several strongly electronically coupled, covalently bound chromophores. An exemplary base chromophore unit described herein is perylene, which has a $T_1$ energy of roughly 1.51 eV and an $S_1$ energy in solution of 2.8 eV. The synthesized perylene-containing multichromophoric structures may have a singlet fission (SF) endothermicity of many times $k_BT$, even as the $S_1$ and $T_1$ energies are modified by substitution. Crystalline perylene largely undergoes excimer formation in the excited state due to strong 7-stacking. To avoid such deleterious chromophore interactions perylene units were covalently linked into oligomers in a head-to-tail fashion. To ensure exciton delocalization along the oligomer chain, the perylenes were covalently bound with the 1,4-dialkynyl-2,5-bis(ethylhexyloxy)-benzene molecular motif, which imparts strong electronic coupling to the perylene chromophores linked by these units. The resultant exemplary perylene oligomer chemical structures are shown in FIG. 1A. The generalized oligomer structure of the four examples shown in FIG. 1A is summarized below in Structure 1.

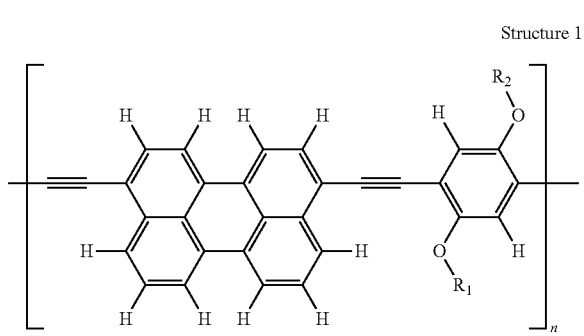

Structure 1

Referring again to the four exemplary oligomers of FIG. 1A and Structure 1, n may be equal to 1, 2, 3, or 4 and $R_1$ and $R_2$ may both be an ethyl substituted hexane group. The four structures shown in FIG. 1A are referred to as 1-OPP, 2-OPP, 3-OPP, and 4-OPP, respectively, in the remainder of this disclosure. Referring again to Structure 1, in some embodiments of the present disclosure, each of $R_1$ and $R_2$ may be a hydrocarbon chain having between 1 and 20 carbon atoms. The hydrocarbon chain may be a straight chain and/or a branched chain and it may be saturated and/or unsaturated. In some embodiments of the present disclosure, $R_1$ and/or $R_2$ may include other elements such as at least one of oxygen, sulfur, nitrogen, and/or phosphorus.

Structure 1 can be generalized to the Structure 2 below.

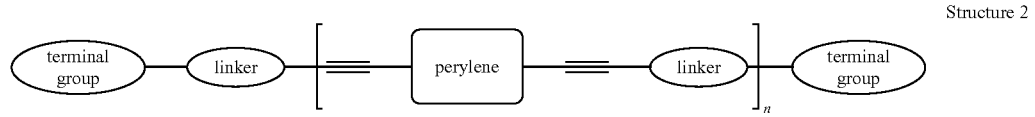

Structure 2

Thus, according to some embodiments of the present disclosure, an oligomer may include a repeat unit constructed of a perylene group (i.e. chromophore) positioned between two carbon-carbon triple bonds and a linker group. Further, the oligomer may be capped with a terminal group, which may or may not also include a linker group. The oligomer may contain between 1 and 20 repeat units, i.e. $1 \leq n \leq 20$.

Examples that fall within the scope of the present disclosure of the perylene group are summarized below in Scheme 1. Examples of linker groups are summarized in Scheme 2. Examples of terminal groups are summarized in Scheme 3.

Scheme 1

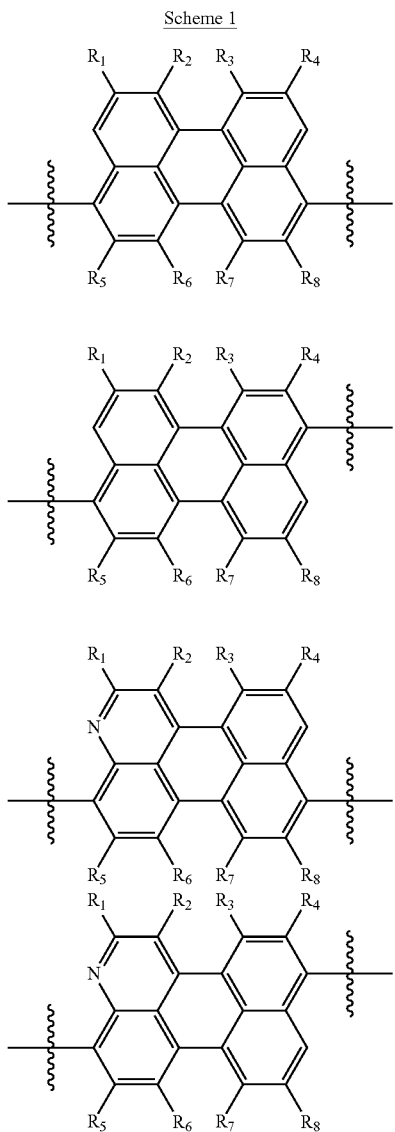

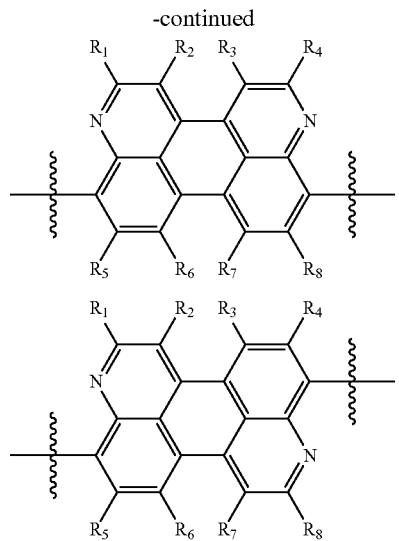

Scheme 2

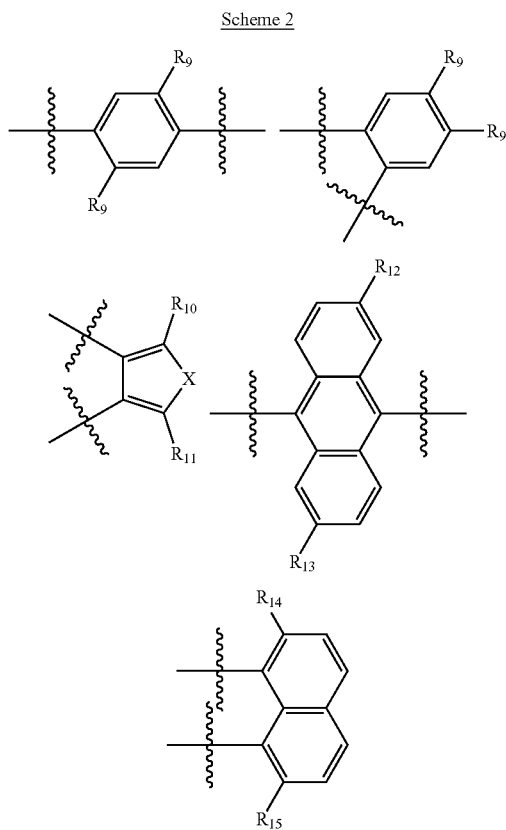

Scheme 3

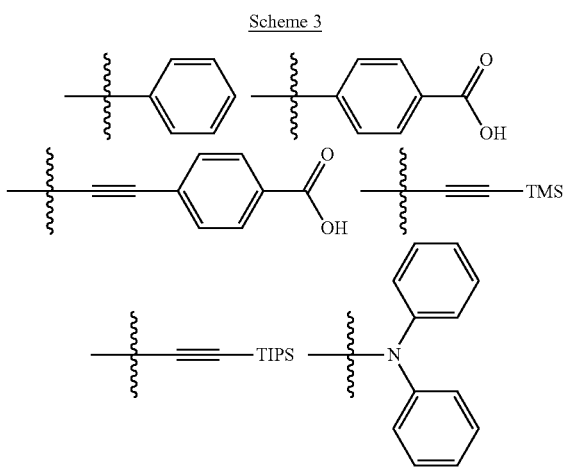

Scheme 4

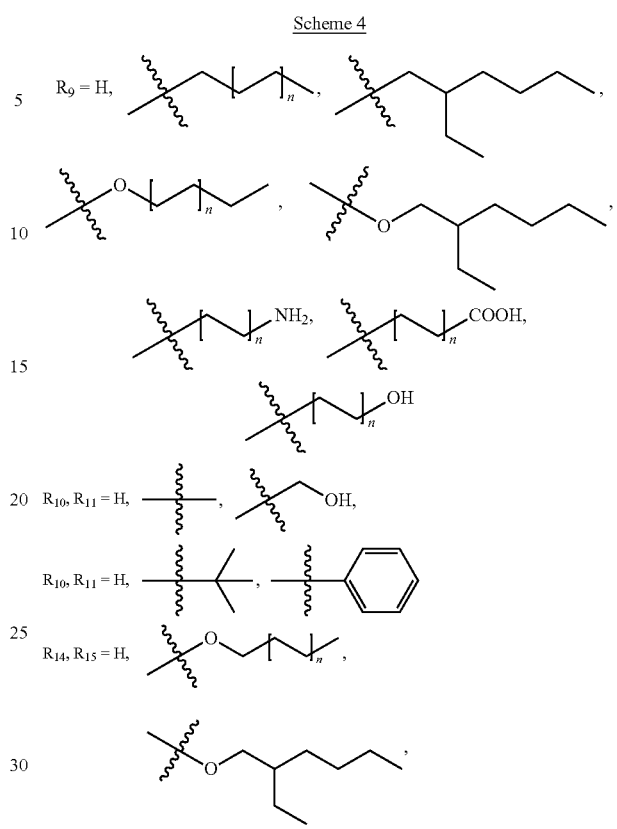

Referring to Scheme 1 for the perylene group, each of $R_1$, $R_2$, $R_3$, $R_4$, $R_5$, $R_6$, $R_7$, and/or $R_8$ may include at least one of a hydrogen atom, a fluorine atom, or a hydrocarbon chain having between 1 and 20 carbon atoms. Each of $R_1$, $R_2$, $R_3$, $R_4$, $R_5$, $R_6$, $R_7$, and/or $R_8$ may be the same functional group or different functional groups. A hydrocarbon chain may be saturated or unsaturated, linear or branched. Specific examples of hydrocarbon chains, according to some embodiments of the present disclosure include a methyl group, an ethyl group, a propyl group, a butyl group, a pentyl group, and/or a hexyl group, as a branched chain and/or straight chain.

Referring to Scheme 2 for the linker groups, $R_9$ may include a hydrocarbon chain having between 1 and 20 carbon atoms. A hydrocarbon chain may be saturated or unsaturated, linear or branched. Specific examples of hydrocarbon chains, according to some embodiments of the present disclosure include a methyl group, an ethyl group, a propyl group, a butyl group, a pentyl group, and/or a hexyl group, either as a branched chain and/or straight chain. In some embodiments of the present disclosure, $R_9$ may be a hydrocarbon chain that is end-capped with an amine functional group, a carboxylic acid functional group, and/or a hydroxyl group. In some embodiments of the present disclosure, $R_9$ may include an oxygen atom between the aromatic ring of the linker group and the hydrocarbon chain. In some embodiments of the present disclosure, $R_{10}$ and $R_{11}$ may include a hydrogen atom, a methyl group, and/or a methyl group end-capped with a hydroxyl group. $R_{10}$ and $R_{11}$ may be the same functional group or different functional groups. In some embodiments of the present disclosure, $R_{12}$ and $R_{13}$ may include a hydrogen atom, a tert-butyl group, and/or a benzene ring. $R_{12}$ and $R_{13}$ may be the same functional group or different functional groups. $R_{14}$ and $R_{15}$ may include a hydrogen atom and/or functional group constructed of a hydrocarbon chain with an oxygen atom positioned between the hydrocarbon chain and the aromatic group of the linking group. $R_{14}$ and $R_{15}$ may be the same functional group or different functional groups. Referring again to Scheme 2, X may include at least one of an oxygen atom, a sulfur atom, and/or a selenium atom. Scheme 4 below summarizes examples of $R_9$ through $R_{15}$.

Structure 3 illustrates another generalized form of oligomers, according to some embodiments of the present disclosure. "L" represents the linker group described above for Scheme 2.

Structure 3

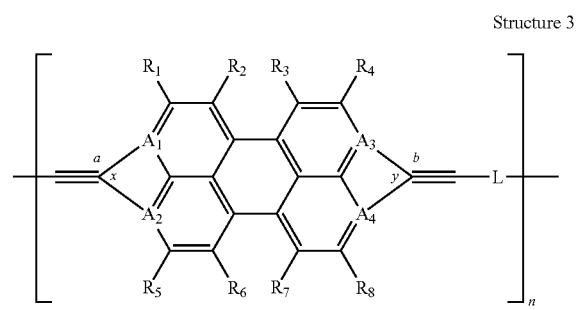

Thus, according to some embodiments of the present disclosure, $A_1$ or $A_2$ may be a nitrogen atom with the other non-nitrogen atom being carbon, or both $A_1$ and $A_2$ may be carbon atoms. Either $A_1$ or $A_2$ may be a carbon atom connected to carbon atom "a" by a single covalent carbon-carbon bond, "x". Similarly, $A_3$ or $A_4$ may be a nitrogen atom with the other non-nitrogen atom being carbon, or both $A_3$ and $A_4$ may be carbon atoms. Either $A_3$ or $A_4$ may be a carbon atom connected to carbon atom "b" by a single covalent carbon-carbon bond, "y". The oligomer of Structure 3 may contain between 1 and 20 repeat units, i.e. $1 \leq n \leq 20$. Examples of $R_1$, $R_2$, $R_3$, $R_4$, $R_5$, $R_6$, $R_7$, and $R_8$ are defined above.

As shown herein, optical excitation produced a delocalized $S_1$ exciton in all exemplary oligomers in solution, but that formation of long-lived triplet excitons was only possible in compounds with three or more coupled chromophores (e.g. perylene-linker group/group repeat units). Whereas the dimer (i.e. 2-OPP) showed no evidence of independent triplets, the pairs of triplet excitons in the trimer (i.e. 3-OPP) and tetramer (i.e. 4-OPP) were generated with yields of about 30% and rise times of a few ns, with lifetimes of ~10 ns, and ~100 µs. From transient absorption analysis at early delay times, one may surmise that relaxation within $S_1$ produces a highly planar oligomer geometry, from which $^1(T_1T_1)$ states form. Without wishing to be bound by theory, one can hypothesize that the reversibility of the formation (as in the dimer), or the succession to independent triplet excitons (as in the trimer or tetramer), may be dictated by the availability of spatially separated and conformationally disordered 2×$T_1$ geometries. In addition to spatial separation of triplet excitons via energy transfer, which has been invoked for non-endothermic SF, this mechanism at least partially relies on distinct torsional potentials in singlet vs. $T_1T_1$ excited states, and the flexibility of covalently bound chromophores to adopt geometries that isolate triplets on relevant timescales. These features represent unique types of entropic contributions, distinct from those found in SF solids that exhibit large singlet delocalization but an otherwise rigid and uniform geometrical and energetic landscape.

As shown herein, connecting chromophores (i.e. perylene groups) with 1,4-dialkynyl-2,5-bis(ethylhexyloxy)-benzene (i.e. linker groups) can result in strong electronic coupling between chromophores, due to favorable orbital overlap through the linker group. However, the phenylalkynyl linker groups also alter the excited state energies of the chromophores to which they are attached. As shown herein, alkyne substitution lowered both the $S_1$ and $T_1$ energies by more than 0.25 eV (see FIG. 1C). Thus, the additional unshared phenyl group on the trimer and tetramer chromophore ends likely reduces the triplet energies with respect to the central chromophore(s) and likely adds an enthalpic contribution to triplet localization. The estimated triplet values of all of the perylene-containing oligomers was about 1.25 eV.

Figure 1B:
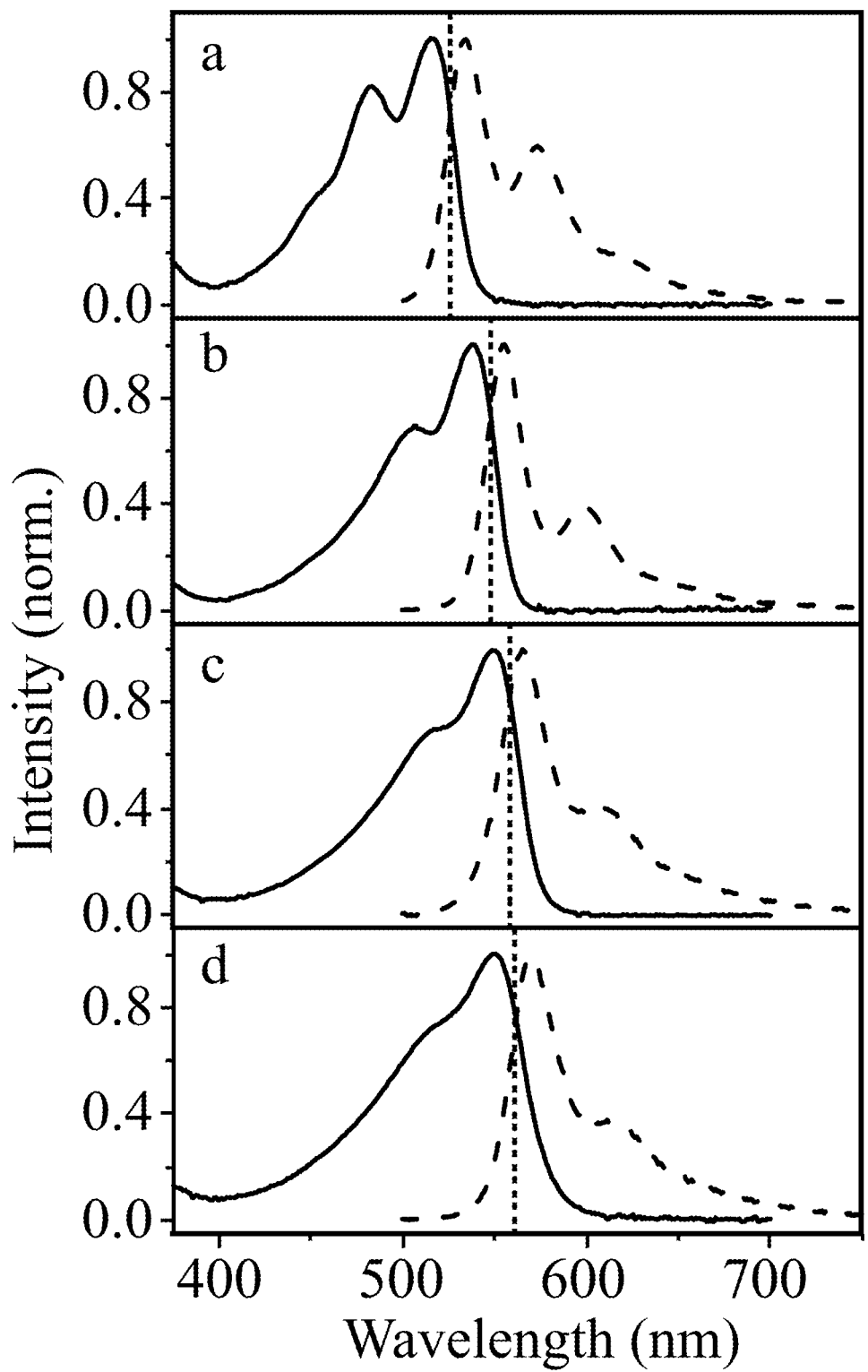
FIG. 1B illustrates absorption and emission spectra of dilute tetrahydrofuran (THF) solutions of a) 1-OPP, b) 2-OPP, c) 3-OPP, and d) 4-OPP, for the corresponding chemical structures shown in FIG. 1A, respectively from top to bottom, according to some embodiments of the present disclosure. Solid lines correspond to absorption spectra and dashed lines to emission spectra.
Figure 1C:
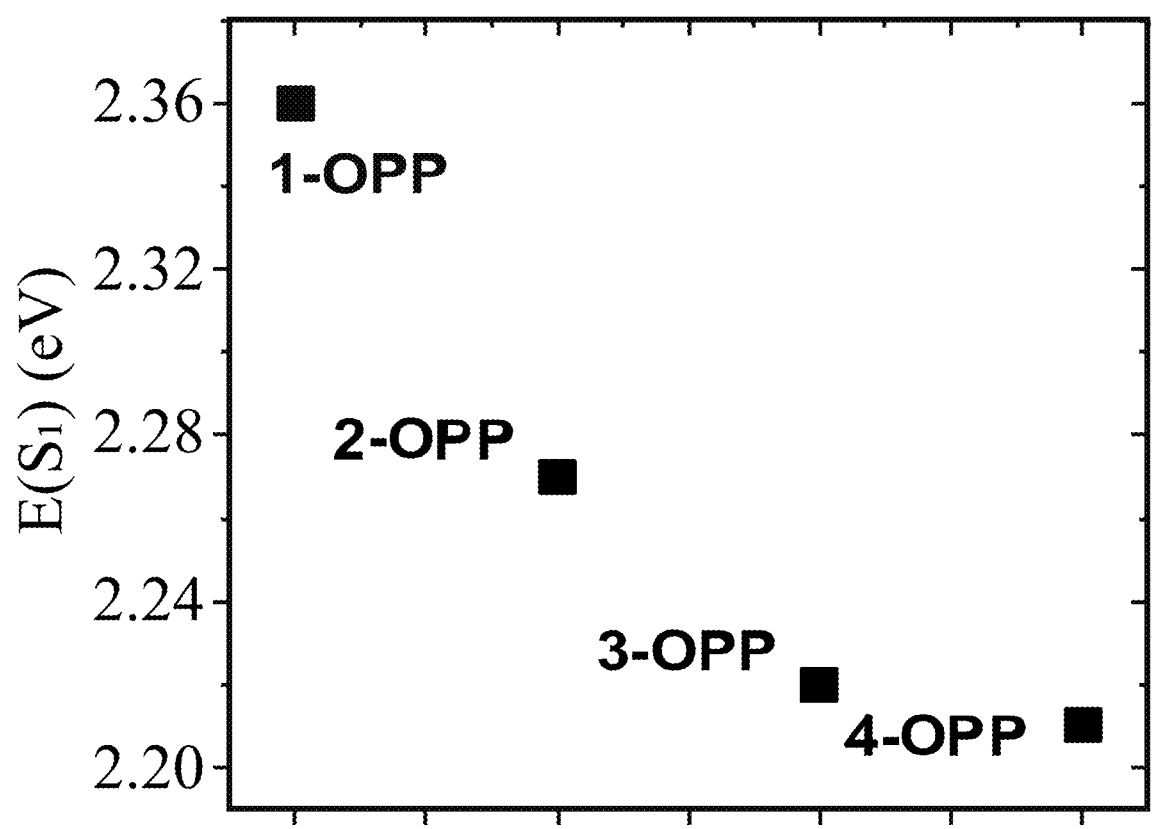
FIG. 1C illustrates $S_1$ energies of perylene oligomers obtained from the crossing point of absorption and emission, according to some embodiments of the present disclosure.
Figure 7:
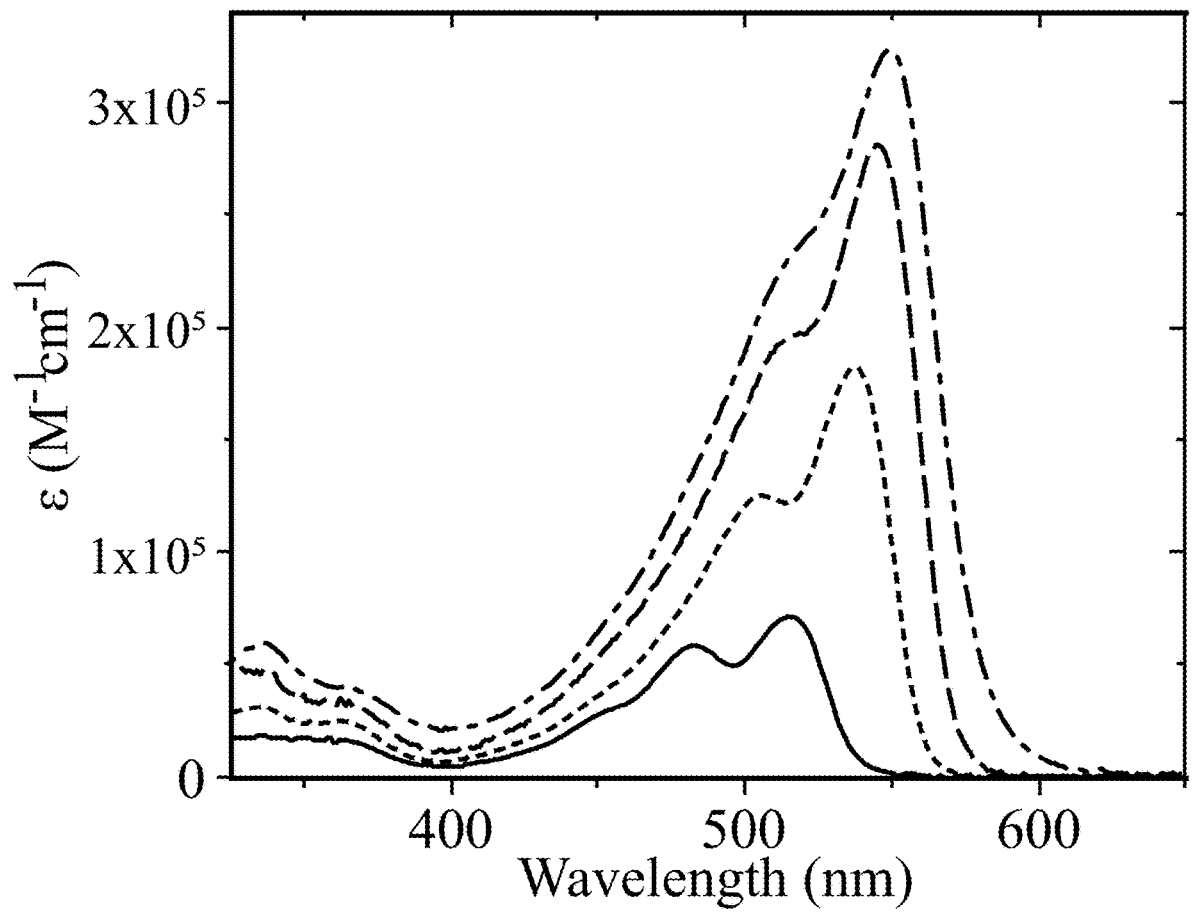
FIG. 7 illustrates extinction coefficients of dilute THF solutions of 1-OPP (solid line), 2-OPP (short dashed line), 3-OPP (long dashed line), and 4-OPP (long dashed-short dashed line), according to some embodiments of the present disclosure.

The magnitude of electronic coupling in our perylene oligomers can be gleaned from linear absorption spectra (see FIG. 1B). The red-shift of dimer (2-OPP) absorption $\lambda_{max}$ relative to that of the monomer (1-OPP) is 23 nm (0.11 eV), and subsequent addition of a chromophore resulted in a trimer (3-OPP) absorption red-shifted from that of the monomer by 33 nm (0.15 eV). The absorption of the tetramer (4-OPP) is slightly broader than that of the trimer with a 35 nm (0.16 eV) red-shift compared to 1-OPP. The molar absorptivities of these compounds also increased with increasing oligomer length and reached values of >$10^5$ $M^{-1}cm^{-1}$ (see FIG. 7). $\lambda_{max}$ is summarized below in Table 1.

TABLE 1

Molar absorptivity/extinction coefficients of dilute THF solutions of 1-OPP, 2-OPP, 3-OPP, and 4-OPP.

| | $\lambda_{max}$ (nm) | log ε @ $\lambda_{max}$ (log $M^{-1}cm^{-1}$) |
|---|---|---|
| 1-OPP | 515 | 4.9 ± 0.1 |
| 2-OPP | 538 | 5.3 ± 0.1 |
| 3-OPP | 545 | 5.4 ± 0.1 |
| 4-OPP | 550 | 5.5 ± 0.1 |

While the emission spectra of the oligomers followed a similar redshift pattern to that of the absorption, the intensity of the emission decreased with increasing oligomer length, as shown in Table 2. Based on the geometry of these oligomers, one may expect the transition dipole moments to couple head-to-tail intramolecularly and result in enhanced radiative rates ($k_r$) with respect to the monomer (analogously to molecular aggregates and covalent dimers with similar transition dipole arrangements). The decrease in prompt emission lifetime with increasing oligomer length reflects faster radiative rates; however, the decrease in PLQY for longer oligomers suggests increasing non-radiative decay rates in these compounds. Shorter oligomers have similar radiative rates, however, the large decrease of PLQY in long oligomers reflects slower $k_r$ and faster $k_{nr}$.

TABLE 2

Photophysical data for perylene oligomers in dilute THF solutions.

| | $E(S_1)$ [eV] | $\Phi_{fl}$ | $\tau_{fl}$ [ns] | $T_1$ yield | $k_r$ [$ns^{-1}$] | $k_{nr}$ [$ns^{-1}$] |
|---|---|---|---|---|---|---|
| 1-OPP | 2.36 | 0.86 ± 0.05 | 2.12 ± 0.01 | — | 0.41 | 0.06 |
| 2-OPP | 2.27 | 0.76 ± 0.04 | 1.28 ± 0.01 | — | 0.59 | 0.20 |
| 3-OPP | 2.22 | 0.66 ± 0.05 | 1.01 ± 0.01 | 0.3 ± 0.1 | 0.65 | 0.34 |
| 4-OPP | 2.21 | 0.46 ± 0.02 | 0.88 ± 0.01 | 0.3 ± 0.1 | 0.52 | 0.61 |

Figure 2:
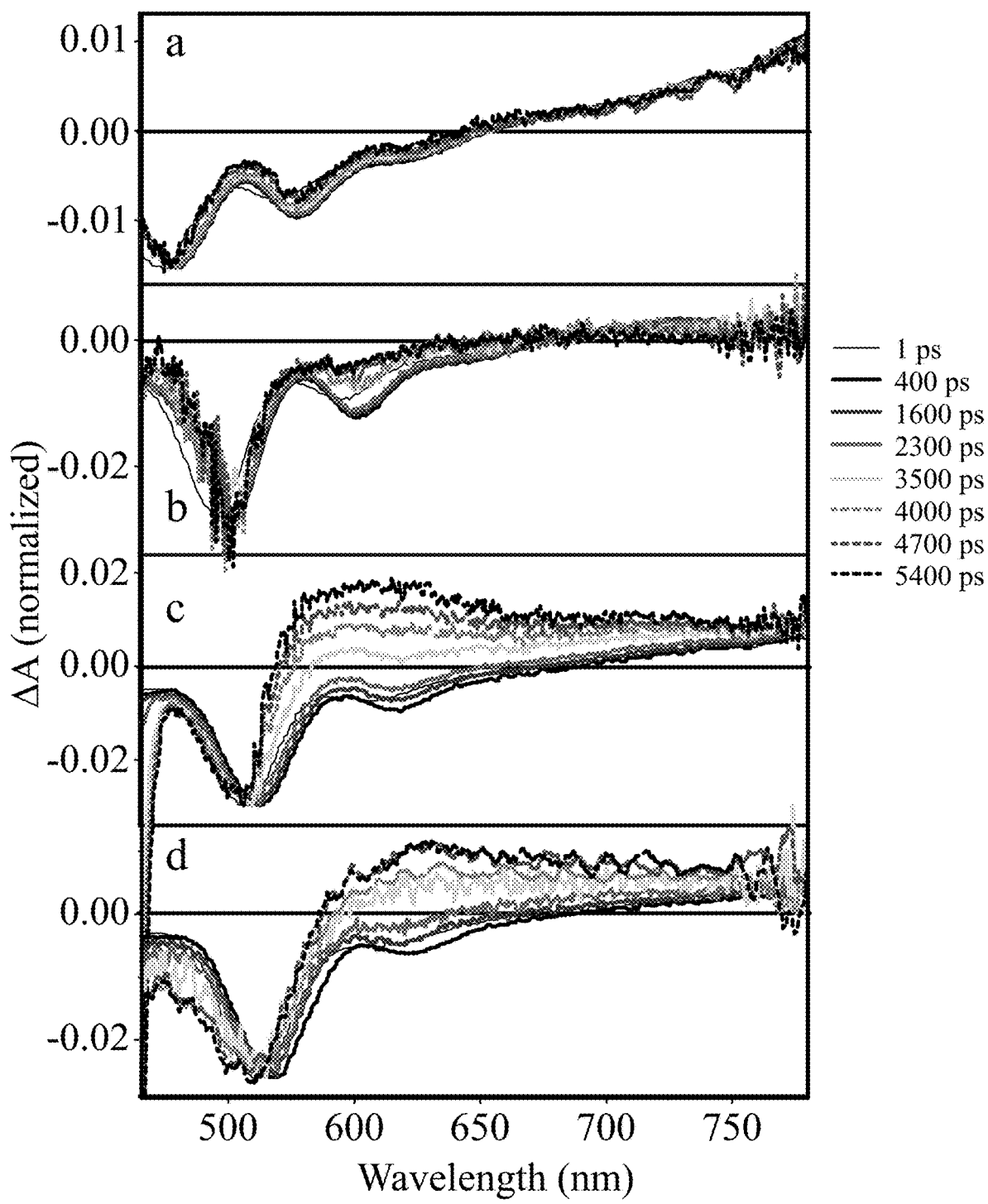
FIG. 2 illustrates femtosecond transient absorption spectra of dilute THF solutions of a) 1-OPP, b) 2-OPP, c) 3-OPP, and d) 4-OPP excited at 500 nm and normalized at the GSB for a time delay up to 5.4 ns, according to some embodiments of the present disclosure.

Referring to FIG. 2, the normalized femtosecond transient absorption (fsTA) spectra of oligomers in solution provide insight into the nature of the non-radiative decay in these systems. All four oligomers exhibited ground state bleach (GSB) (520-550 nm), stimulated emission (SE) (550-620 nm) and $S_1 \rightarrow S_n$ induced absorption (red of 700 nm) in similar spectral regions, as well as a small red-shift of the stimulated emission (SE) up to 400 ps. This red-shift is representative of dynamic molecular planarization, in which the oxyphenyls align with the perylenes, producing the most delocalized excitation upon relaxation. Further evidence for this planarization is found in the steady-state optical data (see FIG. 1B), in which fluorescence spectral bands are narrower than absorption bands, signifying a favored emitting geometry despite many accessible ground state conformations. After 400 ps in 1-OPP, the GSB and SE recover concurrently with $S_1 \rightarrow S_n$ decay, without significant spectral evolution. While 2-OPP still exhibits predominantly $S_1$ spectral features at 5.4 ns, the transient absorption spectra of 3-OPP and 4-OPP evolve to form a state with low intensity broad absorption features in the 550-800 nm spectral range, and residual GSB at 550 nm.

Figure 3:
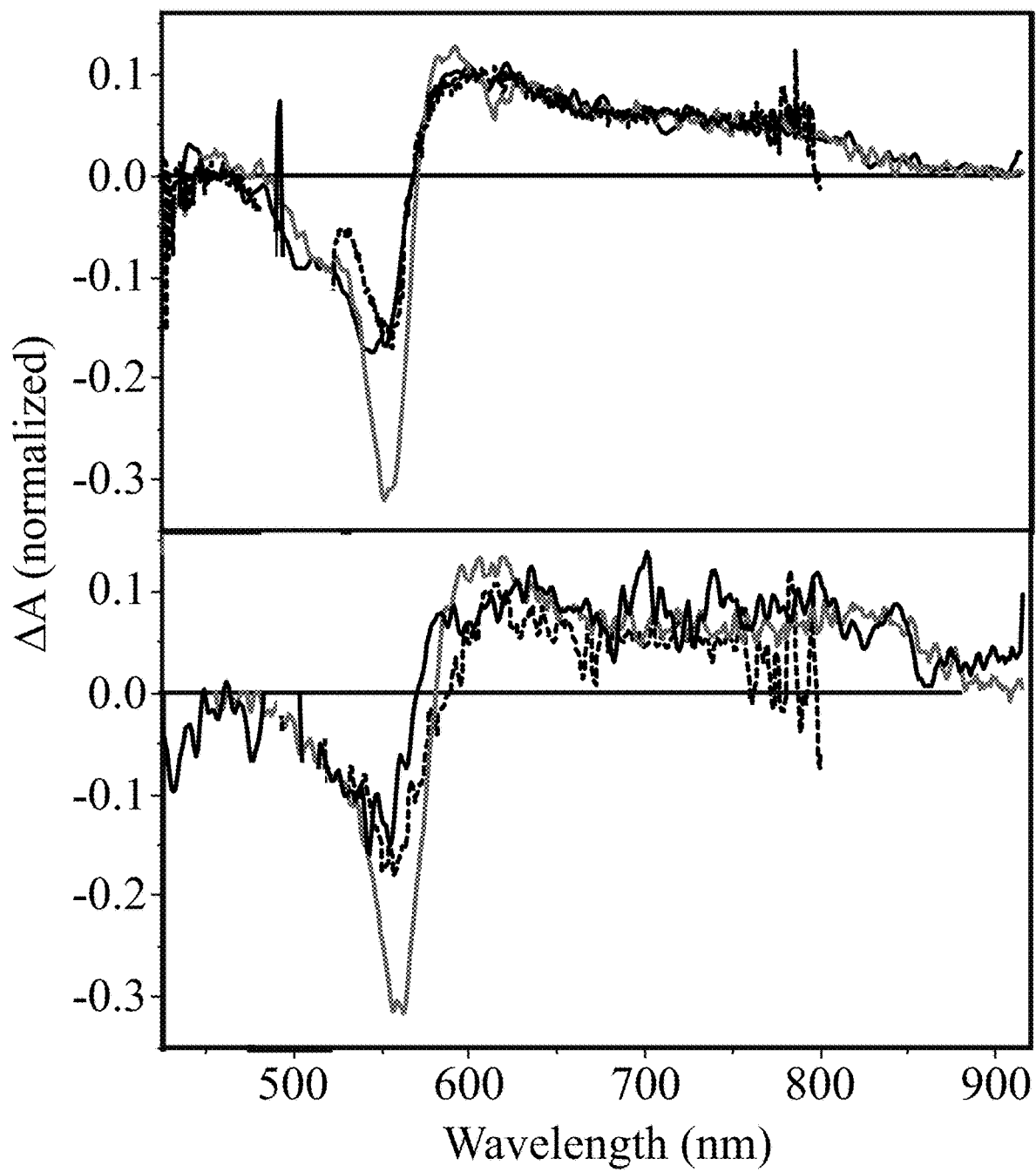
FIG. 3 illustrates spectral overlap of the sensitized induced triplet absorption (top, grey line 3-OPP; bottom, grey line 4-OPP), the >5 ns transient absorption from nsTA of 3-OPP (top, dashed line) and 4-OPP (bottom, dashed line) in a dilute THF solution, as well as the 5.4 ns transient absorption trace from fsTA of 3-OPP (top, solid line), and 4-OPP (bottom, solid line), according to some embodiments of the present disclosure. Tetraphenylporphyrin ($H_2$TPP) and PtTPBP were used as a sensitizers and produced identical triplet spectral shapes; the solutions of the sensitizer and oligomers were excited at 655 nm ($H_2$TPP) or 612 nm (PtTPBP).
Figure 8:
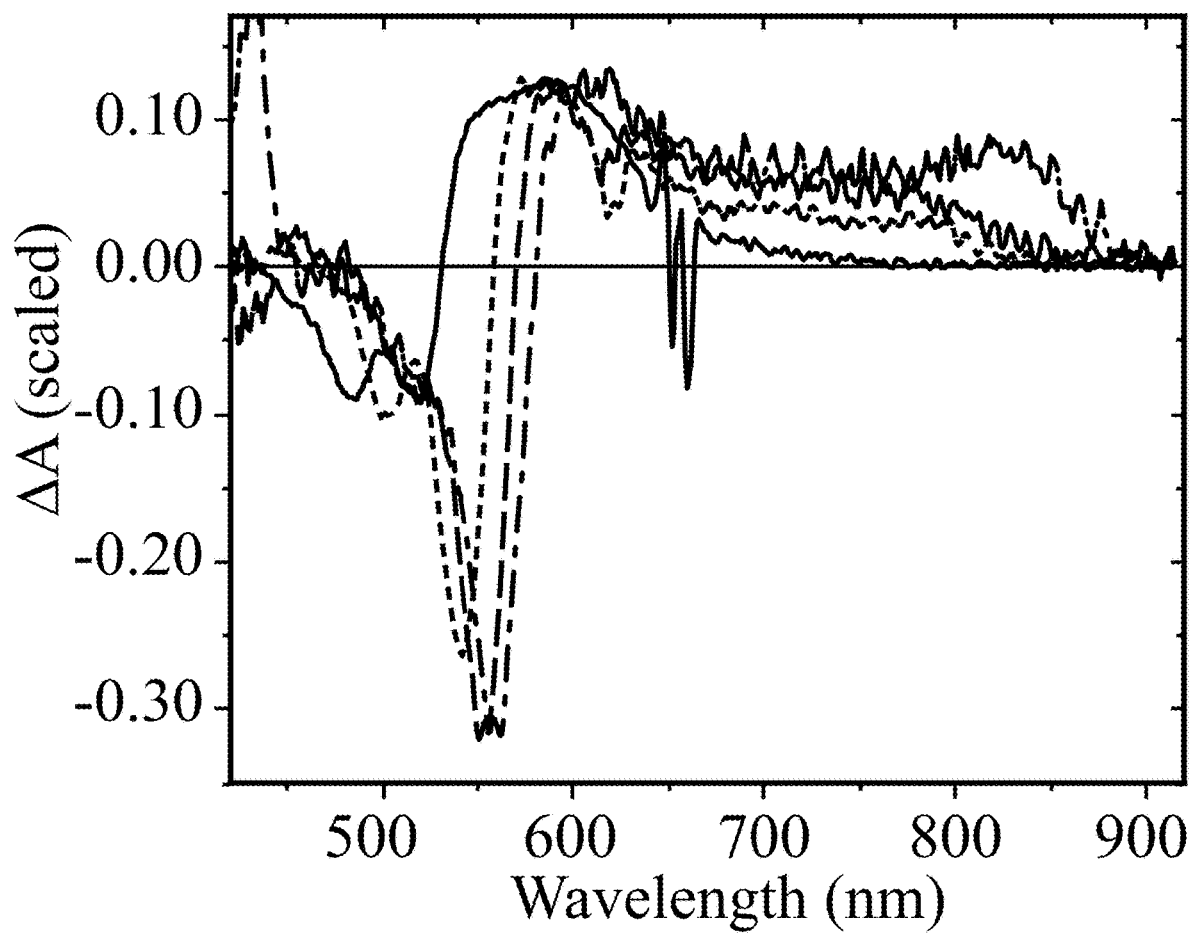
FIG. 8 illustrates sensitized T1 induced absorption spectra of 1-OPP (solid line), 2-OPP (short dashed line), 3-OPP (long dashed line), and 4-OPP (long dashed-short dashed line) in dilute THF solutions, according to some embodiments of the present disclosure. $H_2$TPP and PtTPBP were used as T1 sensitizers.
Figure 9:
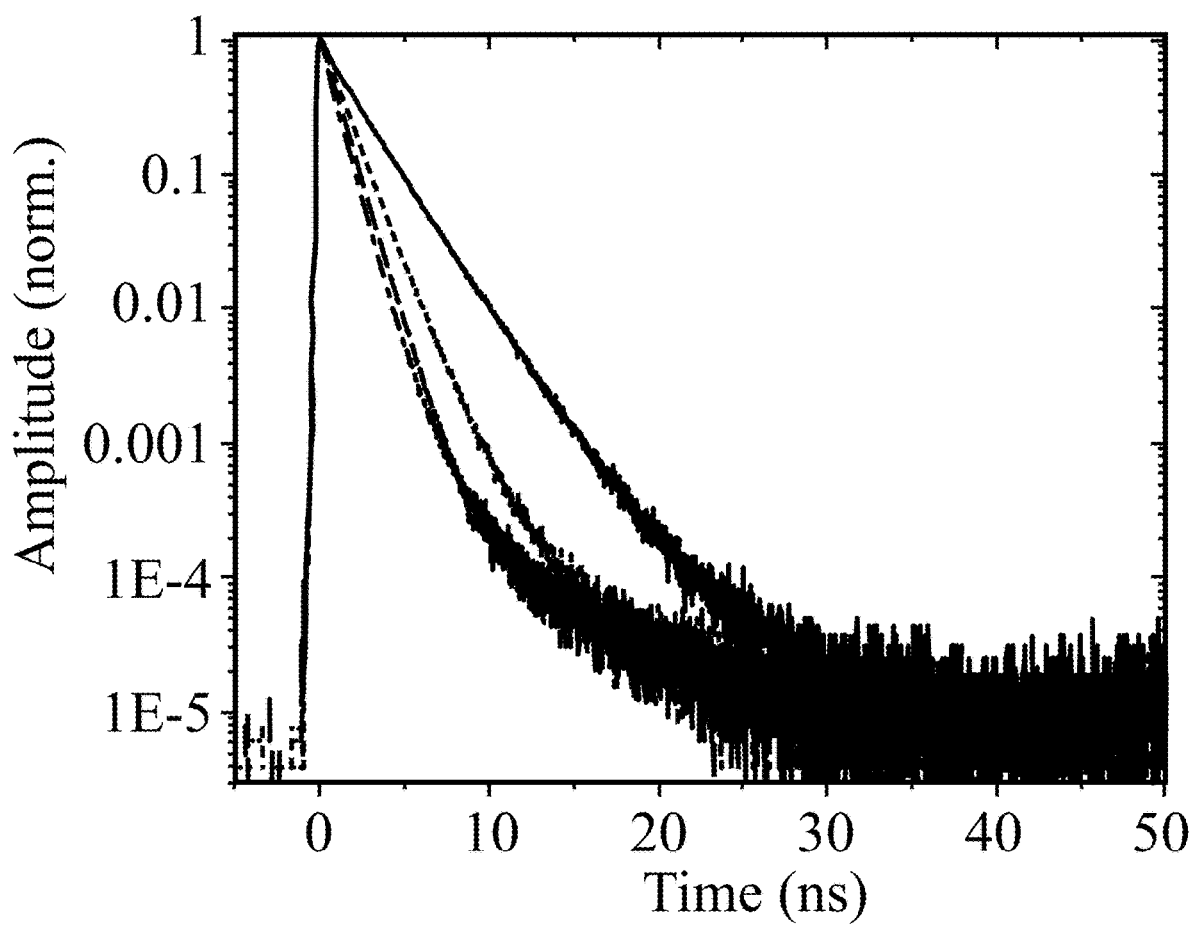
FIG. 9 illustrates fluorescence decays of dilute THF solutions of 1-OPP (solid line), 2-OPP (short dashed line), 3-OPP (long dashed line), and 4-OPP (long dashed-short dashed line), according to some embodiments of the present disclosure.

The long-lived state in 3-OPP and 4-OPP can be assigned as a triplet variant through the close correlation between the sensitized triplet absorption spectra and the >5 ns time slice from direct excitation of these molecules (see FIG. 3). A closer look at the overlaid sensitized $T_1$ spectra with those produced by direct excitation reveals a difference in the relative amplitudes of the GSB and positive induced absorption intensities. In 3-OPP the negative intensity of the GSB of the triplet spectrum produced by direct excitation is half that of the sensitized $T_1$, meaning that per unit of GSB, direct excitation of the oligomers produces twice the intensity of $T_1$ photo-induced absorption compared with that of sensitization, in which only one $T_1$ exciton is imparted to the oligomer. Along with the demonstration of full ground state bleach for each oligomer upon sensitization (see FIG. 8), the doubled relative intensity of $T_1 \rightarrow T_n$ indicates that direct excitation generates a $T_1T_1$ state. Additionally, a small delayed fluorescence component was observed for 2-OPP, 3-OPP, and 4-OPP, which further supports the notion of $^1(T_1T_1)$ formation (see FIGS. 9 and 10A-10D).

Figure 4:
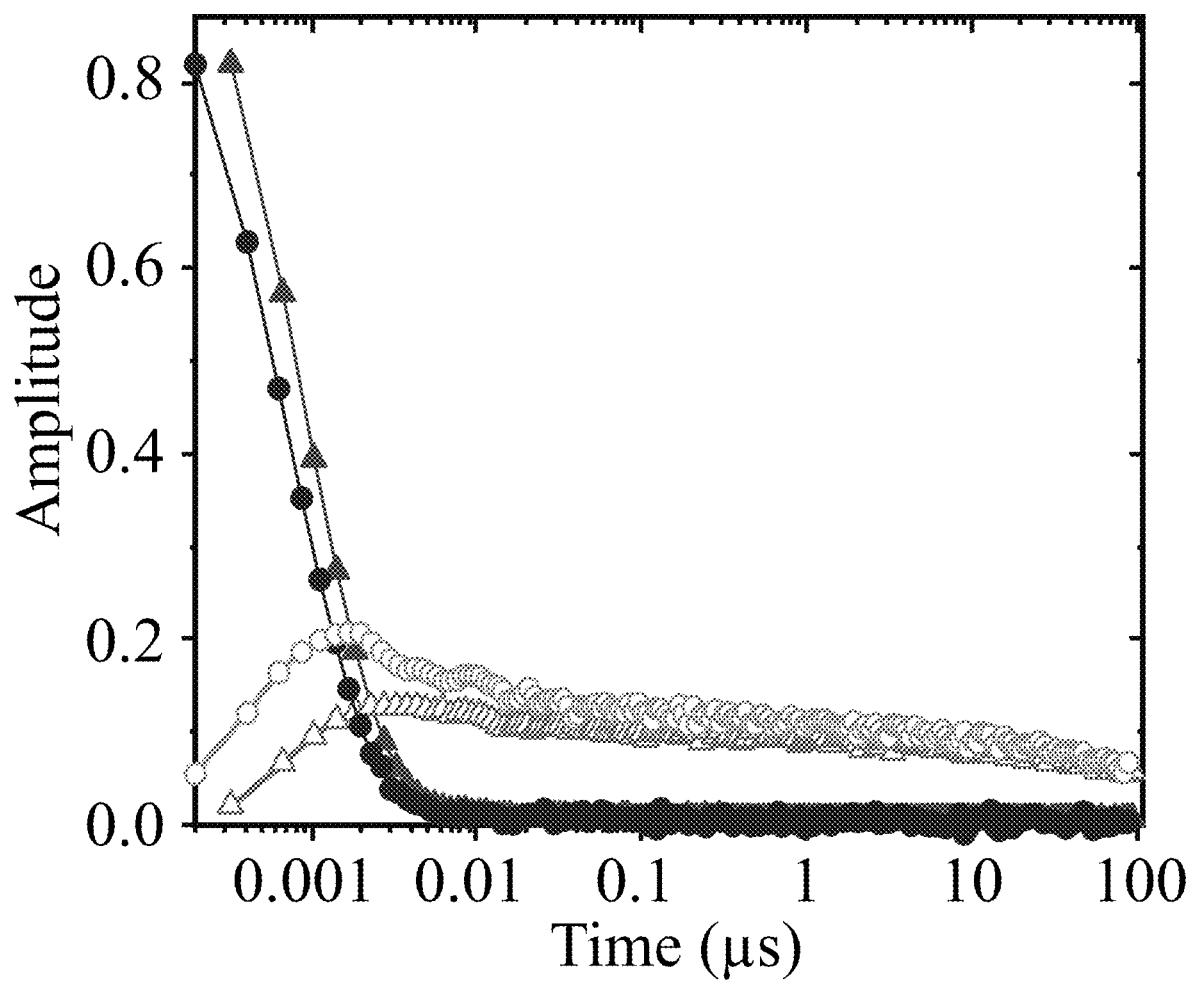
FIG. 4 illustrates ns-µs kinetics of the $S_1$ (solid shapes) and $^1(T_1T_1)$ (open shapes) states of 3-OPP (triangles) and 4-OPP (circles) obtained from singular value decomposition of the nanosecond transient absorption data of dilute solutions of these compounds excited at 500 nm, according to some embodiments of the present disclosure.

To determine the dynamics of the $^1(T_1T_1)$ state in 3-OPP and 4-OPP transient absorption spectroscopy was used with time delays beyond 5 ns. Using singular value decomposition (see FIG. 4) of nsTA data, the populations of the $S_1$ and $T_1T_1$ states were obtained. In both compounds the $T_1T_1$ population decays with two time scales: ~10 ns and ~100 µs. A kinetic model that describes these two decays is discussed below.

Figure 5:
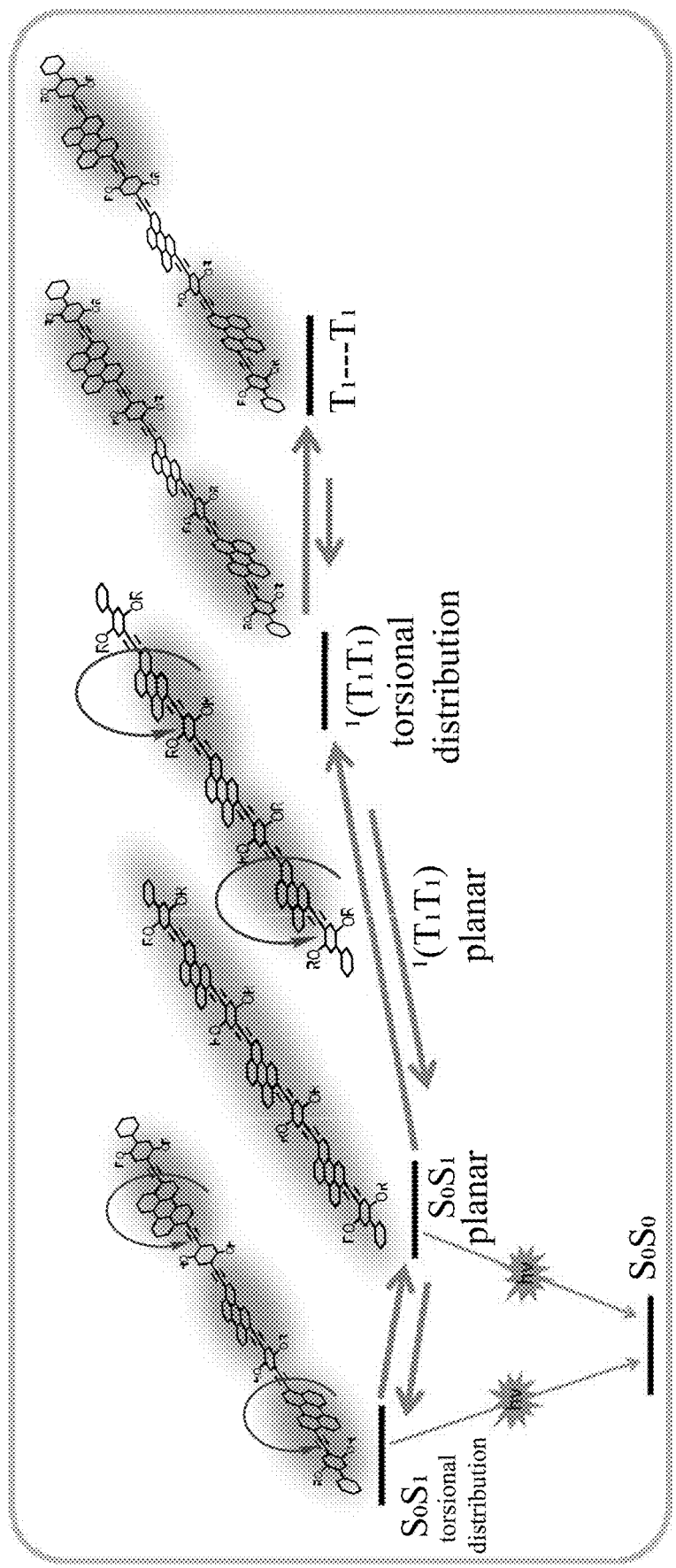
FIG. 5 illustrates a kinetic model of endothermic SF for a dimer versus oligomers, showing planarization in the $S_1$ state followed by torsional disorder in the (TT) states, according to some embodiments of the present disclosure.

Combining insights from fsTA and nsTA, a comprehensive conceptual kinetic model of the excited state dynamics in our oligomers was constructed (see FIG. 5). In this model, it is proposed that excited state planarization is the first process occurring in all compounds. Resulting planar configuration maximizes the electronic coupling between chromophores, such that in the dimer and larger molecules the planar conformation serves as a gateway between $S_1$ and $^1(T_1T_1)$ states, and subsequent torsional distortions break up the electronic coupling between the triplets, thereby prolonging the lifetime of this state. In the dimer, where spatial separation of the $^1(T_1T_1)$ pair is not possible and only two chromophores need to be aligned to achieve the planar configuration, the probability of such structures is high, and annihilation to the lower lying $S_1$ state is more likely. In the trimer and tetramer, the triplet excitons can migrate toward the ends (possibly assisted by a triplet energy gradient), and the probability of aligning three or four chromophores into a planar configuration is much smaller than in the dimer. Therefore, spatial separation of the triplets in the $^1(T_1T_1)$ state prolongs the lifetime of this state, such that it has sufficient time to decorrelate, resulting in even longer-lived triplet pairs.

Figure 6A:
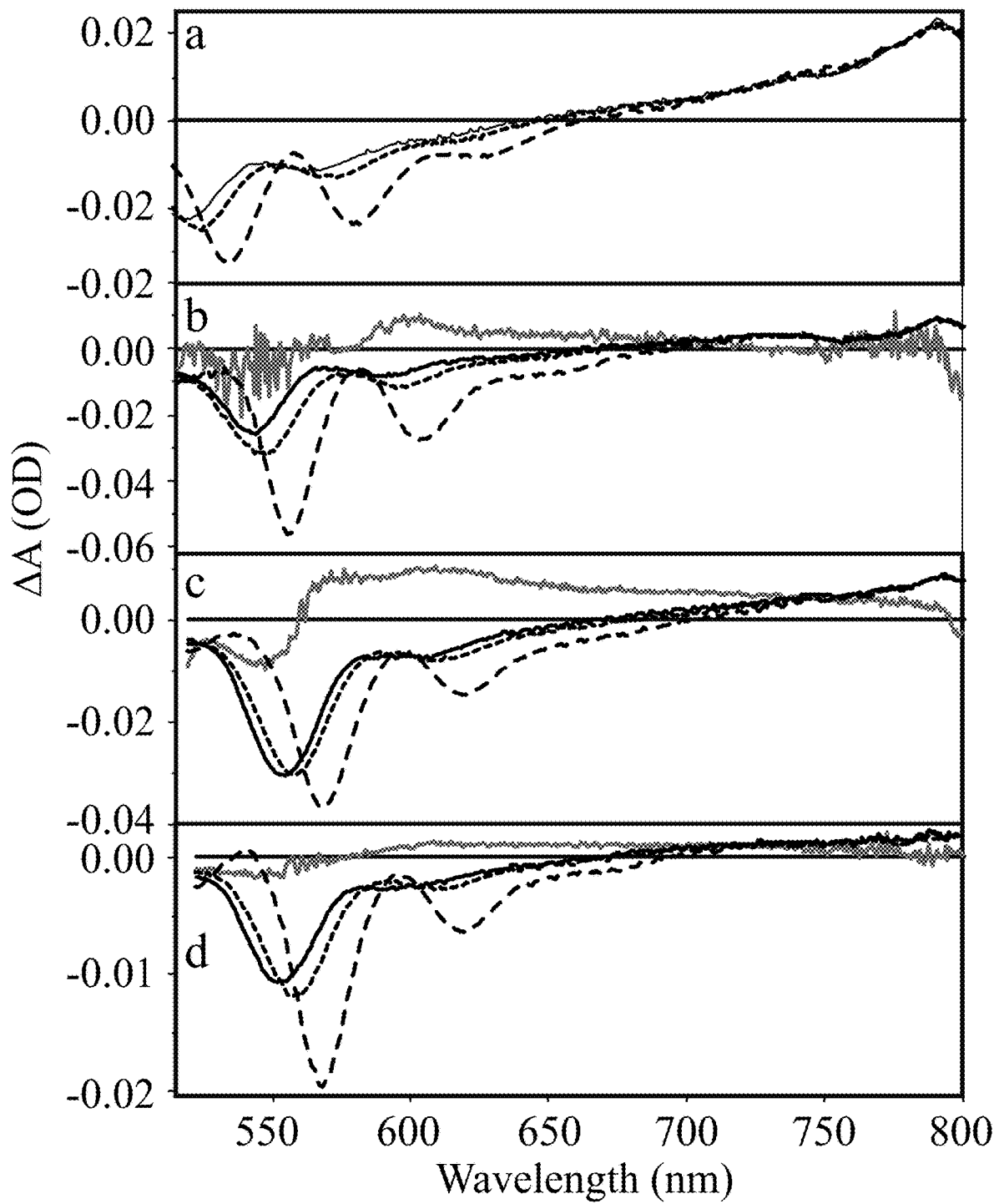
FIG. 6A illustrates evolution associated spectra and population kinetic profiles from fit to fsTA data for a) 1-OPP, b) 2-OPP, c) 3-OPP, and d) 4-OPP, according to some embodiments of the present disclosure. "Final" S1 species—long dashed line; $^1(T_1T_1)$ species—grey line; both the solid black line and the short dashed line correspond to oligomers in an intermediate twisted state.
Figure 6B:
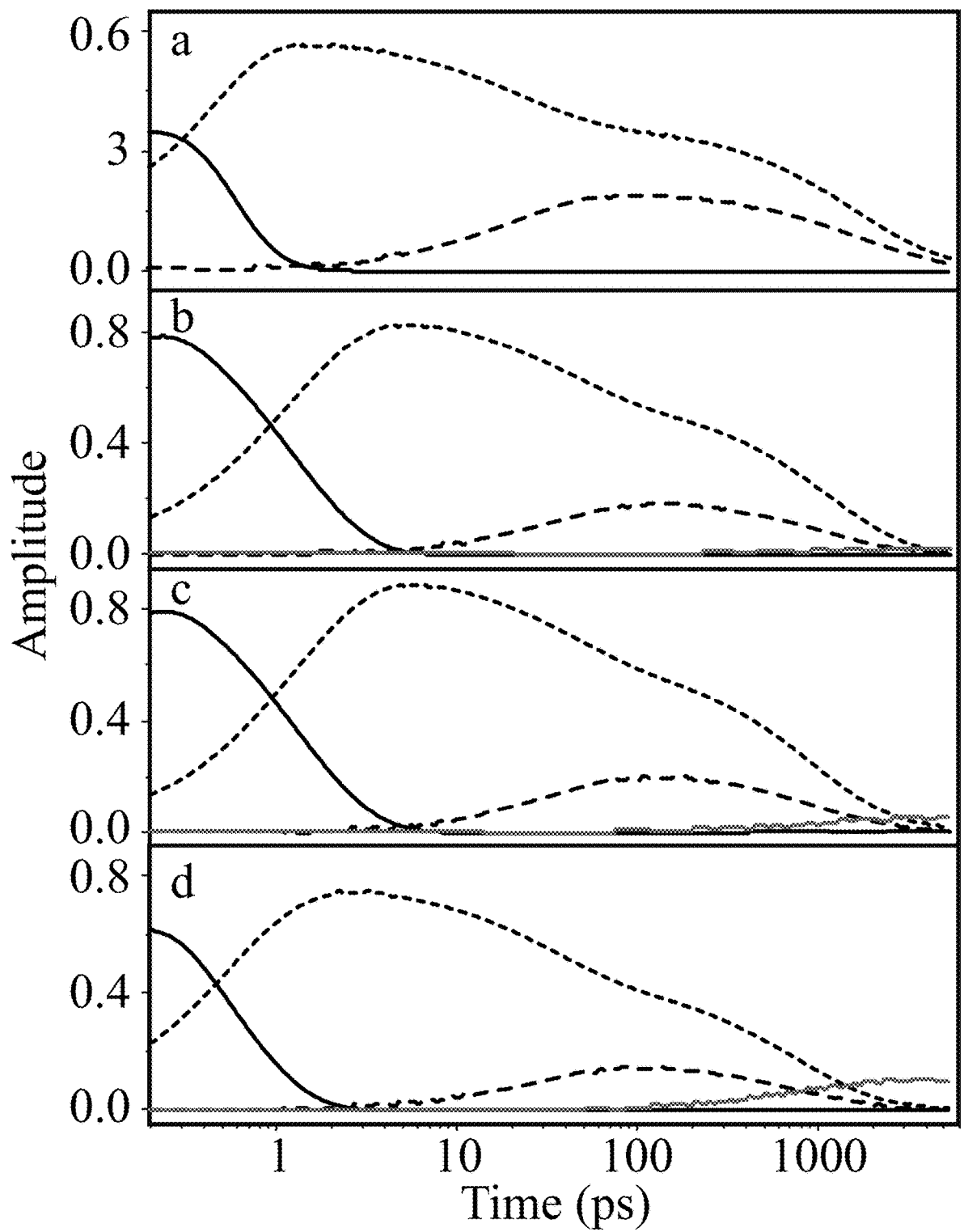
FIG. 6B illustrates population kinetic profiles from fit to fsTA data for a) 1-OPP, b) 2-OPP, c) 3-OPP, and d) 4-OPP, according to some embodiments of the present disclosure. "Final" S1 species—long dashed line; $^1(T_1T_1)$ species—grey line; both the solid black line and the short dashed line correspond to oligomers in an intermediate twisted state.
Figure 10A:
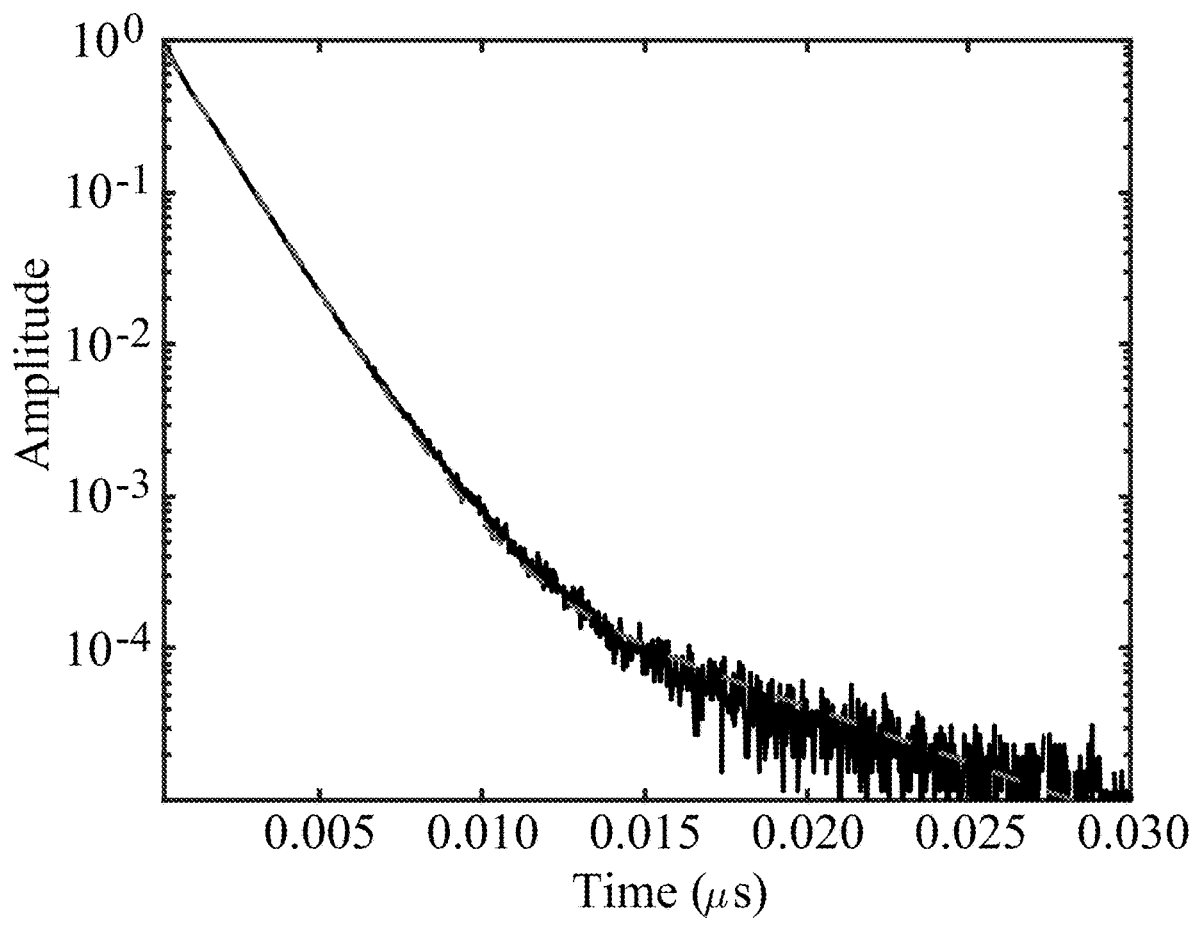
FIGS. 10A-10C illustrate fluorescence decays (solid line) and fits (dashed line), according to some embodiments of the present disclosure.
Figure 10B:
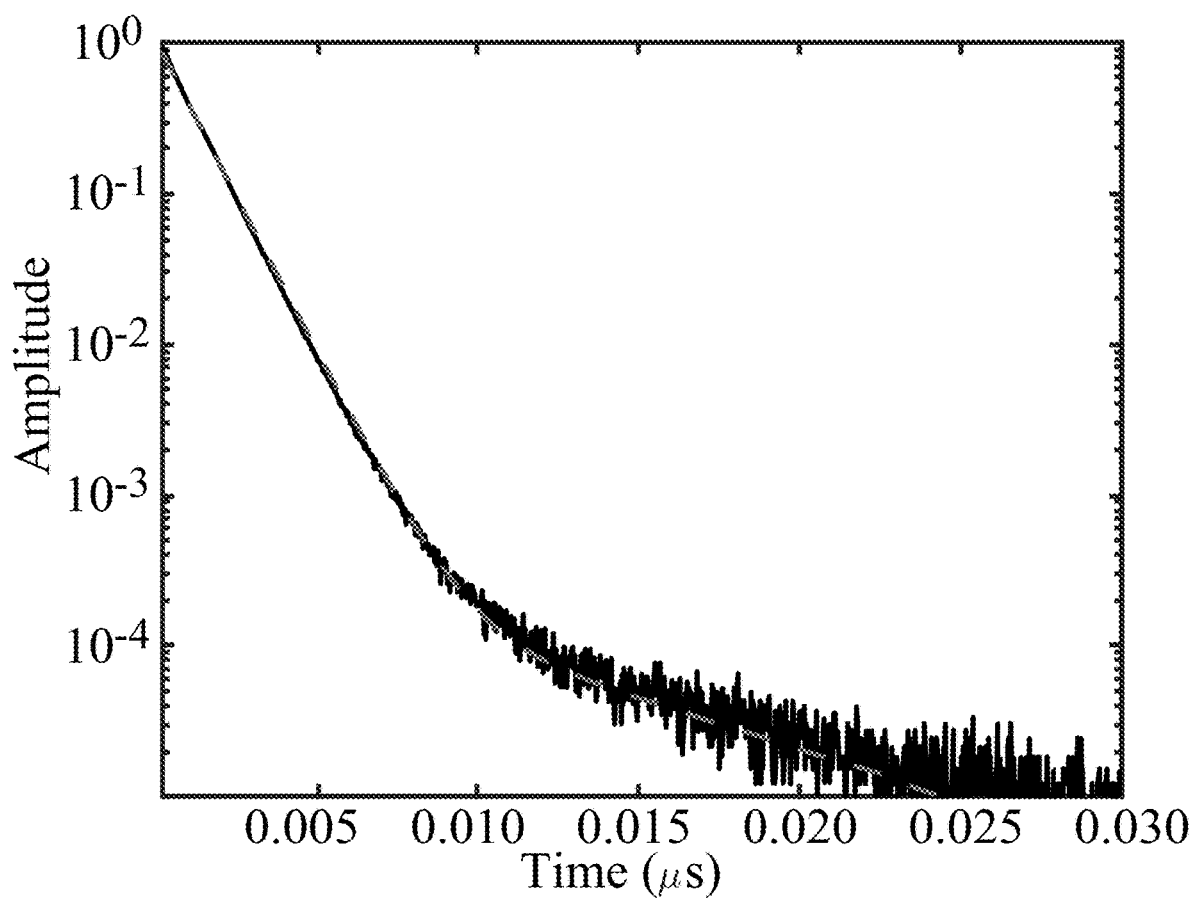
Figure 10C:
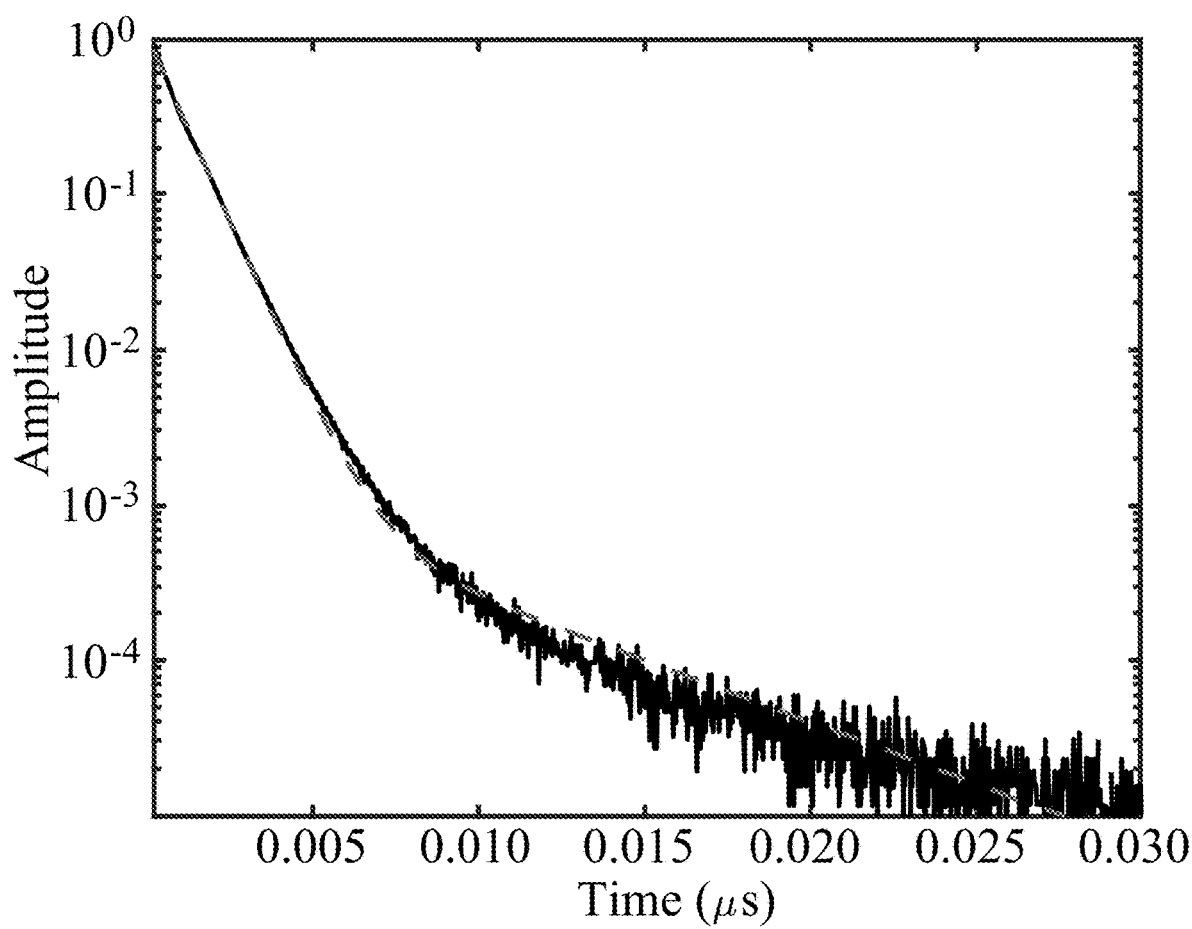
Figure 10D:
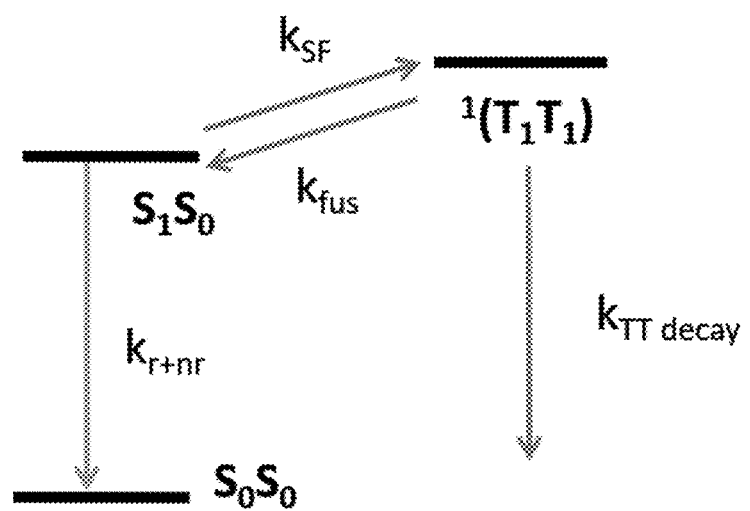
FIG. 10D illustrates a kinetic scheme used to fit the delayed fluorescence, with $k_{TT\ decay}$ set to 0 for 2-OPP, according to some embodiments of the present disclosure.

To solidify the timescales for planarization, fsTA data were fitted with an equilibrium model of four components, shown in FIGS. 6A and 6B with rate constants in Table 3. The spectra (see FIG. 6A) and associated kinetics (see FIG. 6B) reveal the increasing strength and narrowness of stimulated emission over a 20-100 ps timescale, resulting in a "final" $S_1$ species that has the characteristics of a planar chromophore. For 3-OPP and 4-OPP, and to a very minor extent for 2-OPP, this species transformed into the $^1(T_1T_1)$ species identified in nsTA described earlier. The rate of $^1(T_1T_1)$ formation was about twice as fast in 4-OPP compared to 3-OPP), in accordance with the rates derived from delayed fluorescence fits (see FIGS. 10A-10C and Table 4). The decay rates of the $^1(T_1T_1)$ states were beyond the timescale of the fsTA experiments, and nsTA data were used to obtain those rates. Referring to FIGS. 10A-10C, the solid lines represent the measured TCSPC decay rate and the dashed lines represent the mathematical best fit.

TABLE 3

Lifetimes from the fits of concentration dependent fsTA data.

| Lifetimes in ns | 1-OPP | 2-OPP | 3-OPP | 4-OPP |
|---|---|---|---|---|
| $\tau_A$ | 2.4 | 1.9 | 2.4 | 1.4 ± 0.1 |
| $\tau_{AB}$ | 0.00021 | 0.0012 | 0.0013 | 0.0005 ± 0.0003 |
| $\tau_{BA}$ | 86.4 | 35.4 | 5.7 | 9.3 ± 1.9 |
| $\tau_B$ | 1.5 | 1.3 | 2.0 | 1.33 ± 0.08 |
| $\tau_{BC}$ | 0.054 | 0.111 | 0.113 | 0.081 ± 0.025 |
| $\tau_{CB}$ | 0.030 | 0.063 | 0.547 | 0.059 ± 0.003 |
| $\tau_C$ | 2.15 | 0.993 | 0.547 | 0.60 ± 0.02 |
| $\tau_{CD}$ | — | 75.1 | 7.9 | 2.8 ± 0.8 |
| $\tau_{DC}$ | — | 21.0 | 23.2 | 121 ± 161 |

TABLE 4

Fluorescence decay fit parameters (all values in ns−1).

| Rates in ns$^{-1}$ | 1-OPP | 2-OPP | 3-OPP | 4-OPP |
|---|---|---|---|---|
| $k_{radiative+non-radiative}$ | $4.9 \times 10^{-1}$ | $4.9 \times 10^{-1}$ | $8.3 \times 10^{-1}$ | $8.3 \times 10^{-1}$ |
| $k_{SF}$ | — | $2.6 \times 10^{-3}$ | $1.2 \times 10^{-1}$ | $2.7 \times 10^{-1}$ |
| $k_{fus}$ | — | $1.7 \times 10^{-1}$ | $2.9 \times 10^{-3}$ | $4.9 \times 10^{-3}$ |
| $k_{TT\ decay}$ | — | 0 | $1.5 \times 10^{-1}$ | $1.8 \times 10^{-1}$ |

Figure 11:
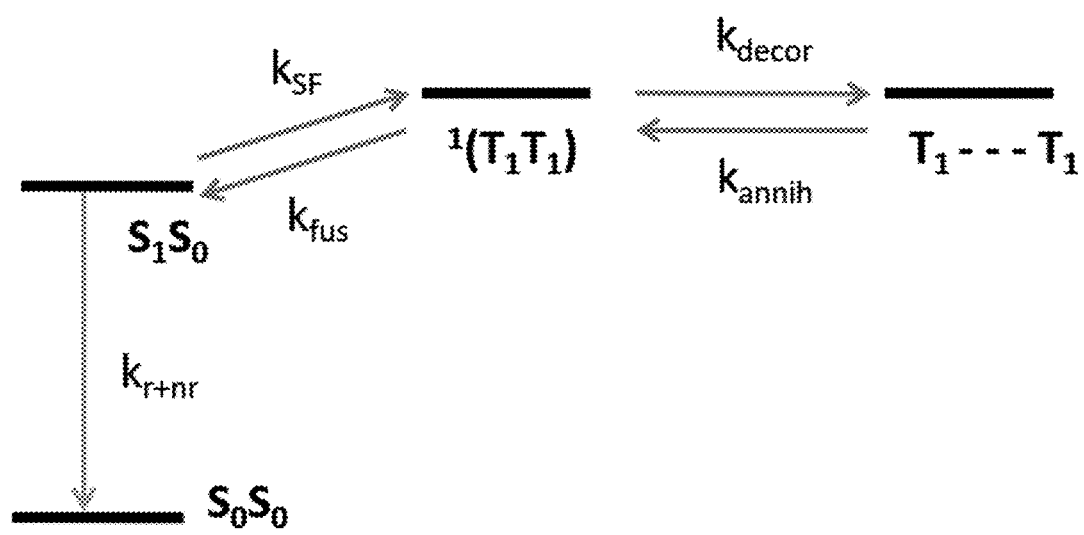
FIG. 11 illustrates a kinetic scheme that was used to model the singlet and $T_1T_1$ populations of 3-OPP and 4-OPP from nsTA data, according to some embodiments of the present disclosure.
Figure 12:
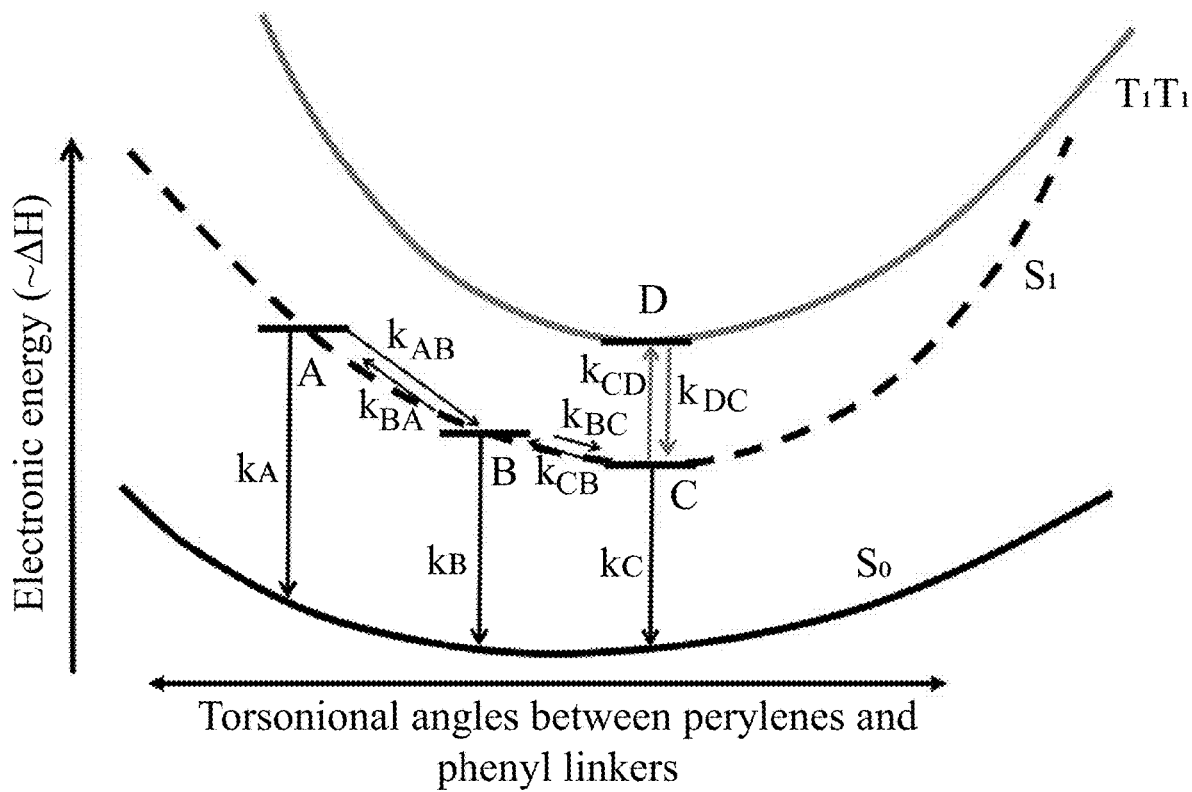
FIG. 12 illustrates a kinetic model used to analyze the fsTA data of the oligomers with target analysis, according to some embodiments of the present disclosure. States A through C correspond to progressively more planar $S_1$ configurations, while State D represents the $^1(T_1T_1)$ state.
Figure 15:
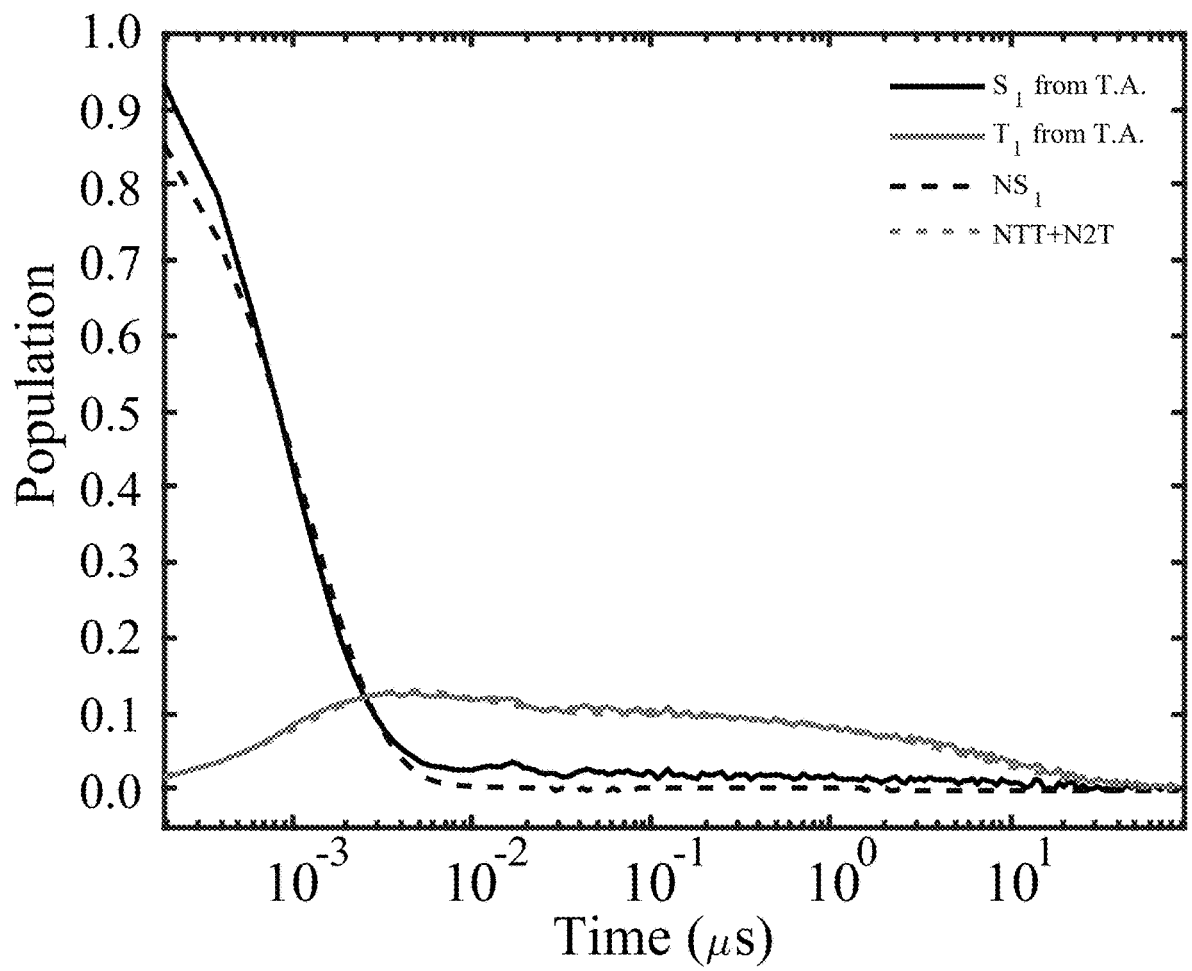
FIGS. 15 and 16 illustrate that a kinetic model described herein accurately accounts for the two time constants of the triplet population decays in 3-OPP and 4-OPP, respectively, according to some embodiments of the present disclosure.
Figure 16:
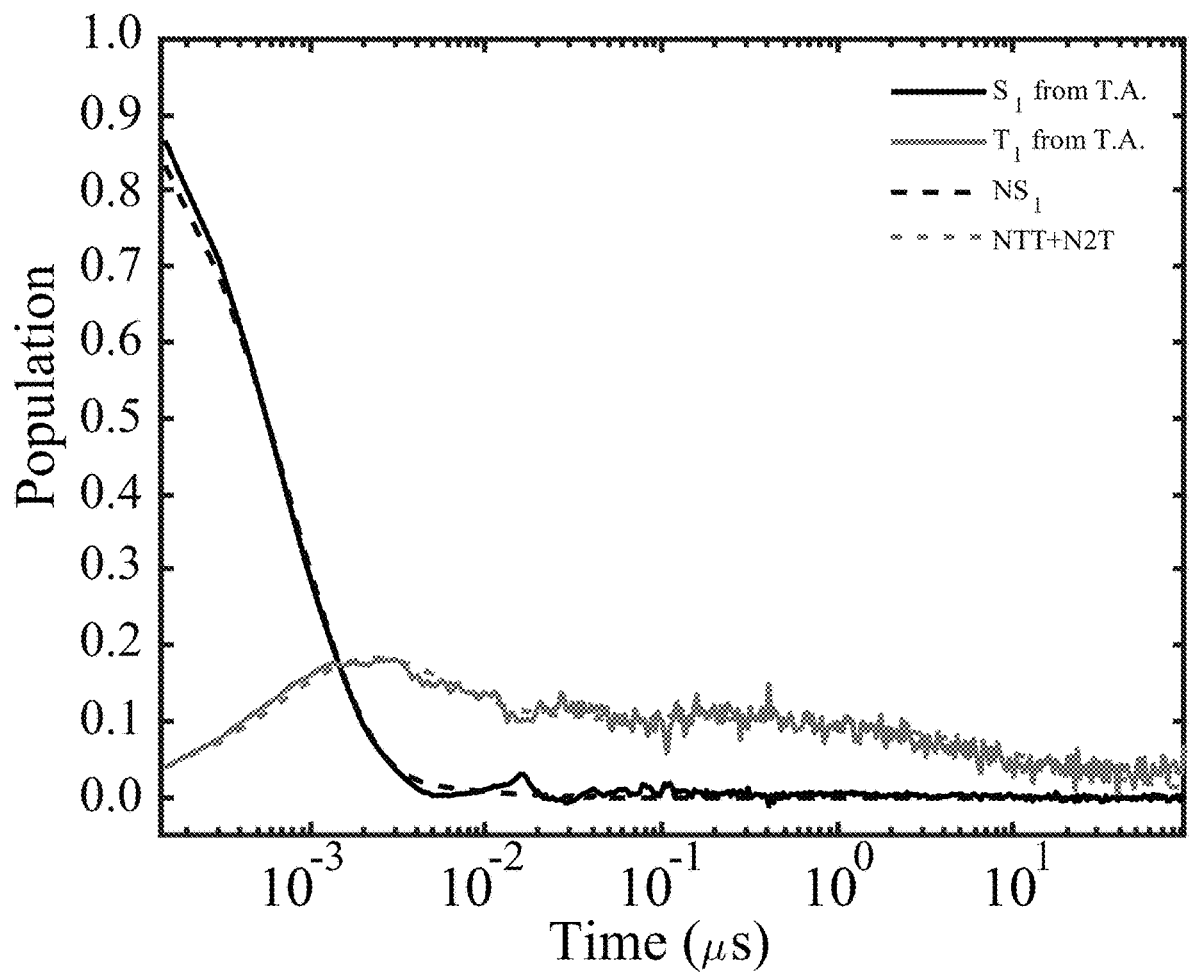

The latter portion of our kinetic scheme, the decay of the $^1(T_1T_1)$ state, was fitted to the nsTA data. The nsTA data has a resolution of ~1 ns, therefore the fast (ps) planarization dynamics were not captured, but only observe the formation and decay of the $^1(T_1T_1)$ state. The long lived $T_1$ signatures were only observed in 3- and 4-OPP, therefore the long-time model was applied to only these compounds. The SVD-derived populations of the $T_1T_1$ reproducibly exhibited a rapid (~10 ns) decay and a long (~100 µs). To account for this behavior, a kinetic scheme was used (see FIG. 11) in which the $S_1$ and $^1(T_1T_1)$ states are in equilibrium connected by the forward ($k_{SF}$) and reverse ($k_{fus}$) rate constants, and the $^1(T_1T_1)$ state is in equilibrium with a longer lived $T_1$---$T_1$ state, connected by forward ($k_{decor}$) and reverse ($k_{annih}$) rate constants. This kinetic model accurately accounts for the two time constants of the triplet population decays in 3-OPP and 4-OPP (see FIGS. 15 and 16), namely the ns timescale of the $^1(T_1T_1)$ state decay, and the microsecond timescale of the $T_1$---$T_1$ state decay. The $k_{SF}$ rate constants obtained from the kinetic model fits (see Table 5 and FIGS. 11 and 12) agree with those from fsTA and delayed fluorescence fits (see Table 4), where the $k_{SF}$ for 4-OPP is about twice as large as that for 3-OPP. The $k_{SF}$>$k_{fus}$ magnitudes in these compounds ($k_{SF}$=1.3×10$^{-1}$ ns$^{-1}$ and $k_{fus}$=4×10$^{-2}$ ns$^{-1}$ for 3-OPP, and $k_{SF}$=3.1×10−1 ns$^{-1}$ and $k_{fus}$=1.4×10−1 ns$^{-1}$ for 4-OPP) indicate that the $^1(T_1T_1)$ state is slightly thermodynamically favored with respect to $S_1$. However, the formation of the $^1(T_1T_1)$ state is enthalpically uphill based on $T_1$ energies of ~1.24 eV if the biexciton binding energy is taken to be small. Therefore, the clear enhancement in long-lived triplet formation in 3-OPP and 4-OPP compared to 2-OPP must result from an entropic gain upon formation of $^1(T_1T_1)$. One can surmise this gain stems from $^1(T_1T_1)$ at equilibrium being best described as a distribution of torsional isomers, with $T_1$ excitons spatially distributed throughout the oligomers (3- and 4-OPP). In this model loss of $^1(T_1T_1)$ occurs upon "geminate" annihilation through the coincidence of planarization (i.e., the $S_1$ geometry) and the presence of triplets on adjacent chromophores. This condition is easily met for 2-OPP but is less likely in 3-OPP and 4-OPP, both due to the large number of torsional isomers and the driving force for triplet localization at the end cap chromophores.

TABLE 5

Rate constants from the fits of concentration dependent nsTA data.

| All rates in ns$^{-1}$ | 3-OPP | | | | 4-OPP | | |
|---|---|---|---|---|---|---|---|
| | C1 | C2 | C3 | Avg | C1 | C2 | Avg |
| $k_{rad+non\text{-}rad}$ | 7.5 × 10$^{-1}$ | 7.1 × 10$^{-1}$ | 7.0 × 10$^{-1}$ | 7.2 × 10$^{-1}$ | 9.6 × 10$^{-1}$ | 9.0 × 10$^{-1}$ | 9.3 × 10$^{-1}$ |
| $k_{SF}$ | 1.3 × 10$^{-1}$ | 1.3 × 10$^{-1}$ | 1.2 × 10$^{-1}$ | 1.3 × 10$^{-1}$ | 2.8 × 10$^{-1}$ | 3.1 × 10$^{-1}$ | 3.0 × 10$^{-1}$ |
| $k_{fus}$ | 3.7 × 10$^{-2}$ | 8.7 × 10$^{-2}$ | 3.3 × 10$^{-2}$ | 5.2 × 10$^{-2}$ | 1.3 × 10$^{-1}$ | 1.4 × 10$^{-1}$ | 1.4 × 10$^{-1}$ |
| $k_{decor}$ | 5.5 × 10$^{-2}$ | 1.3 × 10$^{-1}$ | 6.4 × 10$^{-2}$ | 8.3 × 10$^{-2}$ | 8.5 × 10$^{-2}$ | 8.4 × 10$^{-2}$ | 8.5 × 10$^{-2}$ |
| $k_{annih}$ | 1.5 × 10$^{-4}$ | 6.8 × 10$^{-4}$ | 3.0 × 10$^{-3}$ | — | 1.1 × 10$^{-3}$ | 1.7 × 10$^{-4}$ | — |

Figure 13:
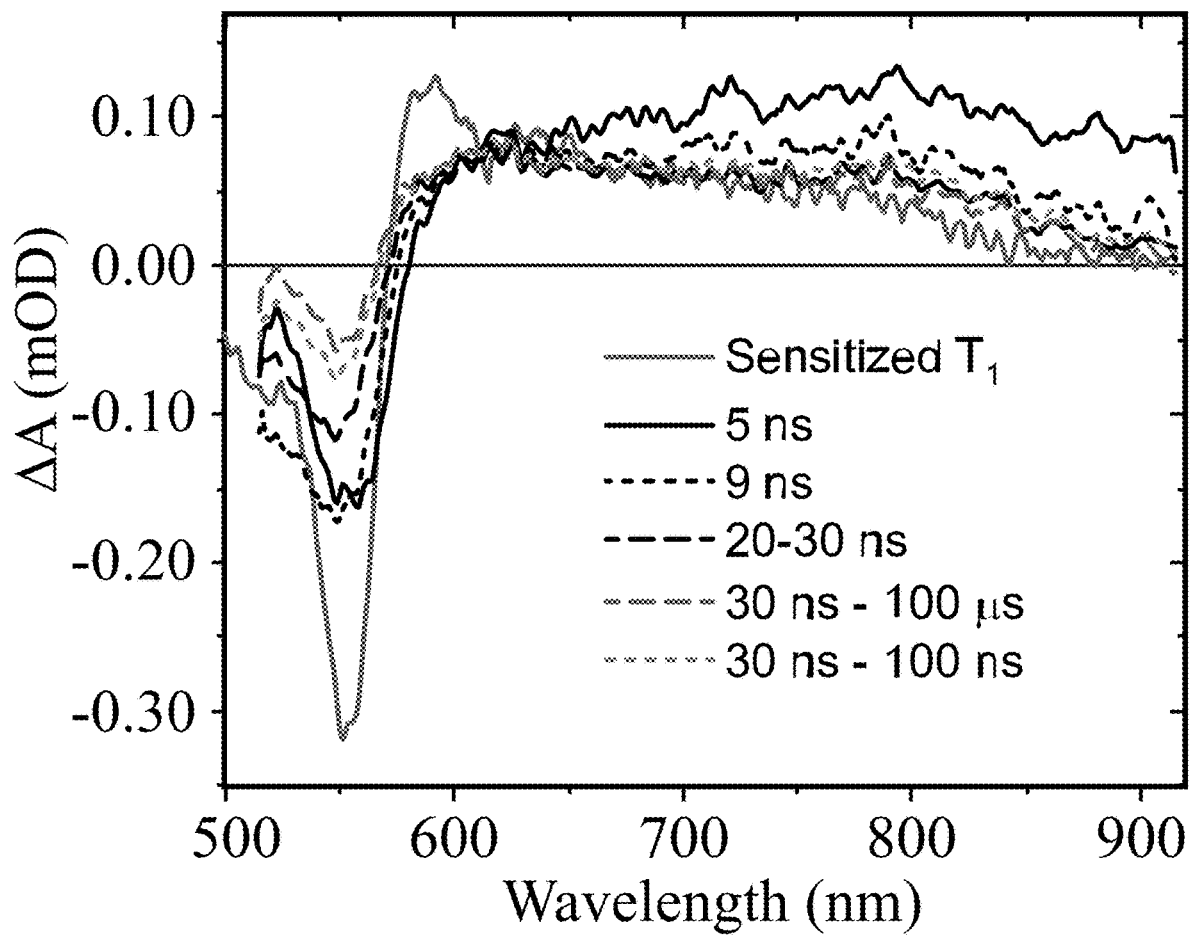
FIG. 13 illustrates the evolution of the nsTA spectra of 3-OPP in THF, according to some embodiments of the present disclosure. The 5 and 9 ns spectra contain a portion of the $S_1$ absorption features. Beyond 20 ns the persistent triplet-like spectrum has a smaller GSB than the sensitized triplet spectrum.
Figure 14:
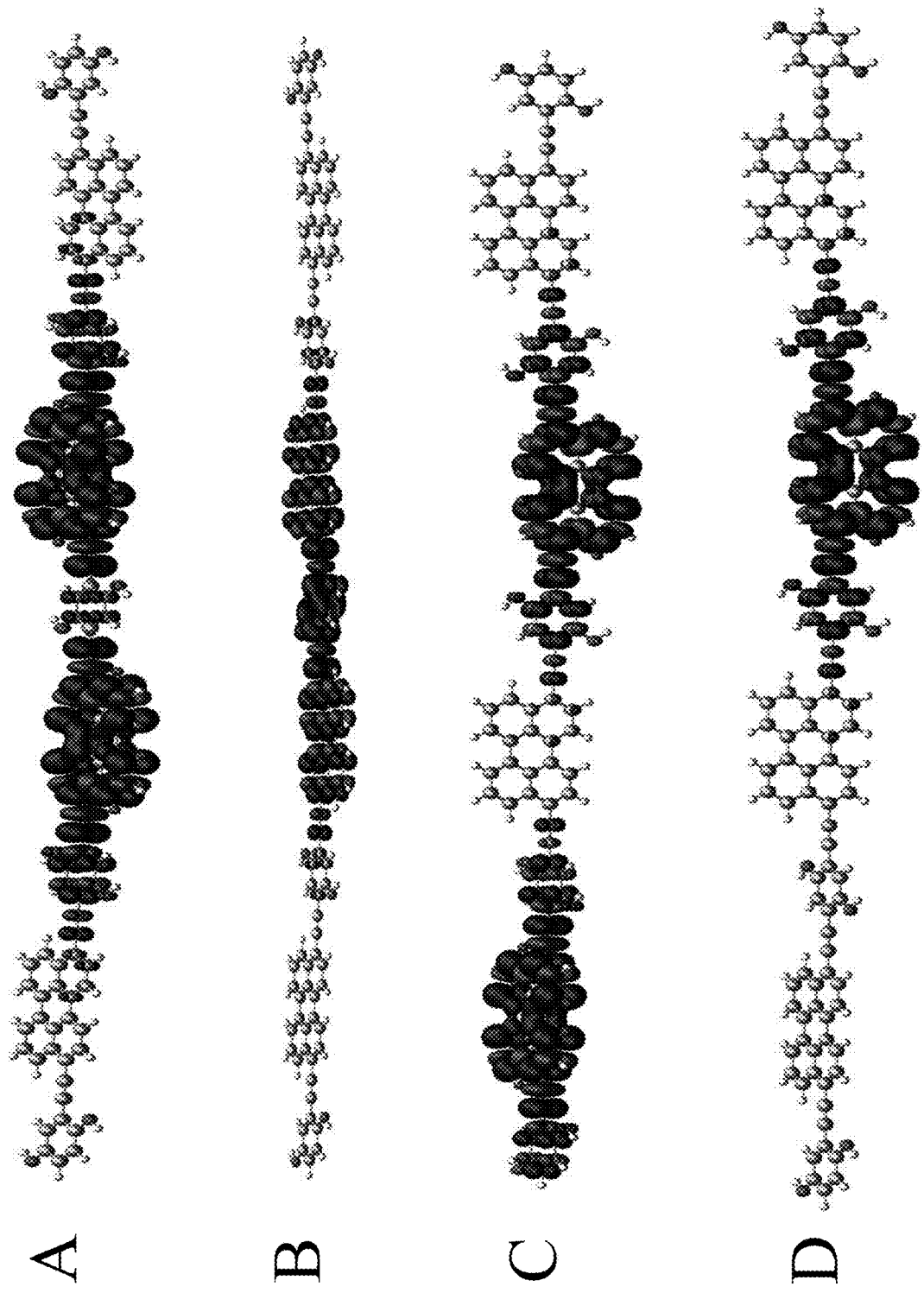
FIG. 14 illustrates triplet and quintet spin distributions in planar and one perylene rotated by 90° 4-OPP, according to some embodiments of the present disclosure. The 5 and 9 ns spectra contain a portion of the S1 absorption features.

The other decay pathway for $1(T_1T_1)$ is to the $T_1\text{---}T_1$ state, which can be envisioned as spatially separated, electronically decoupled, and spin decorrelated triplet pair, thus resulting in its long lifetime. This conversion takes place on similar timescale as previously shown for the decorrelation of $^1(T_1T_1)$. A final state was assigned as $T_1\text{---}T_1$ due to the smaller amplitude of GSB compared to that of the sensitized $T_1$ (see FIG. 13). DFT calculated spin densities of the quintet state in 4-OPP (see FIG. 14) further implicate torsional disorder as the mechanism of triplet separation; in the planar geometry the spin densities occupy nearest neighbor perylenes, while in a 90° twisted geometry, the unpaired spins localize one perylene away from each other. Referring to FIG. 14), "A" an oligomer that is Planar $Q_1$, "B" Planar $T_1$, "C" 90 twisted $Q_1$, and "D" 90° twisted $T_1$.

The key to observation of long-lived triplets appears to lie in the coordinated dynamics of electronic and nuclear processes in oligomers with at least three chromophores. The initial formation of the $S_1$-$^1(T_1T_1)$ equilibrium after photoexcitation is assisted by the ps scale planarization from the Franck-Condon excited state, which has a distribution of conformations due to shallow torsional potentials for twisting about the acetylene linkage in the ground state. The planar $S_1$ geometry, enforced by steep torsional potentials in the cumulenic excited state bonding arrangement produces strong interchromophore coupling and fast SF; however, without subsequent triplet energy transfer and isolation through the regained availability of torsional motions of the $T_1T_1$ state on a 50-100 ps timescale, the equilibrium would be doomed to return to $S_1$ by the endothermic SF situation. The discovery of long-lived triplets despite highly endothermic SF in the trimer and tetramer is undermined somewhat by the relatively low yield, which must at least partially result from competing internal conversion. Understanding and controlling these dynamic and energetic considerations as a function of oligomer structure is a subject of ongoing investigation. Furthermore, increasing the dimensionality of the system by changing the geometry of the oligomers or through aggregate/film formation may provide additional routes for faster SF and increased triplet yield.

In summary, it is demonstrated herein that endothermic SF is enabled in long perylene oligomers with triplet energies ~1.24 eV by the geometric isolation of triplets and torsional disorder, which leads to reduced probability of deleterious annihilation of SF $T_1$ excitons. One may conclude that the strong electronic coupling afforded by diethynyloxybenzene bridges is responsible for fast conversion between the $S_0S_1$ and the $^1(T_1T_1)$ states via SF. However, in dimers without configurations that can sustain spatially separated and electronically decoupled triplets, the thermodynamically favored $S_0S_1$ becomes repopulated and the effective triplet yield is not detectable. Only in longer (trimer and tetramer) oligomers is a significant yield (30%) of long-lived triplets identified and assigned as triplet pairs born from SF. The fundamental insight gained here is a useful starting point for further modifications of supramolecular structures that possess a multitude of high energy triplets that can be used for ultra-efficient photovoltaic or photoelectrochemicalschemes.

EXPERIMENTAL

The following four schemes, Schemes 5-8, illustrate synthesis methods according to some embodiments of the present disclosure.

Scheme 5

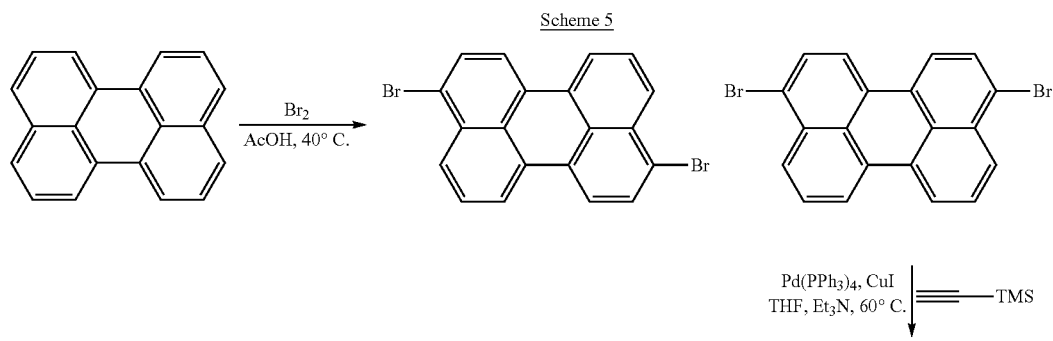

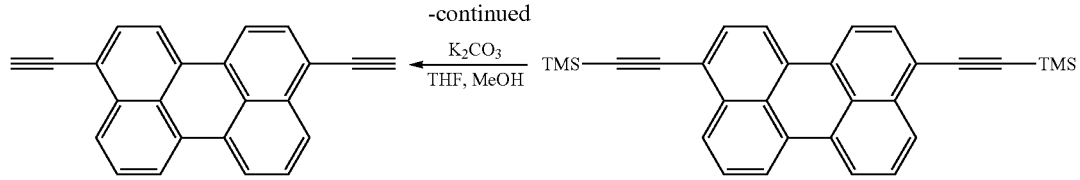
Scheme 6
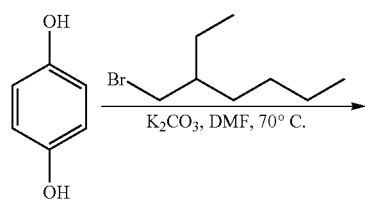
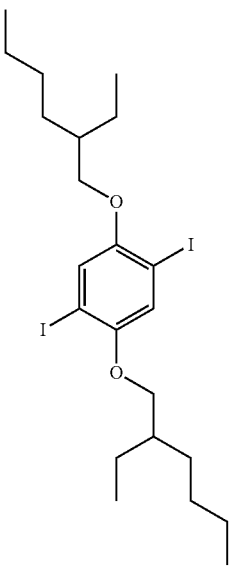
Scheme 7
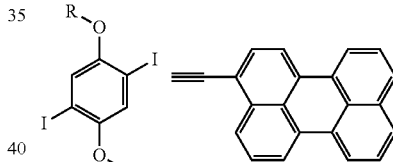
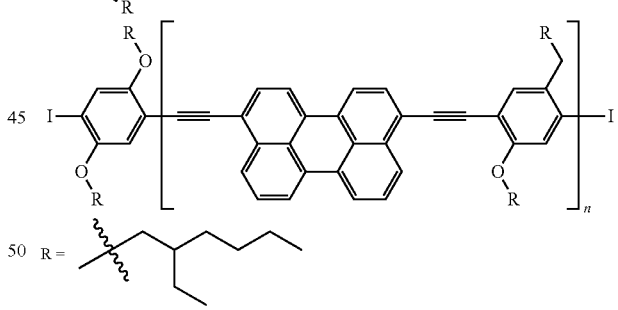
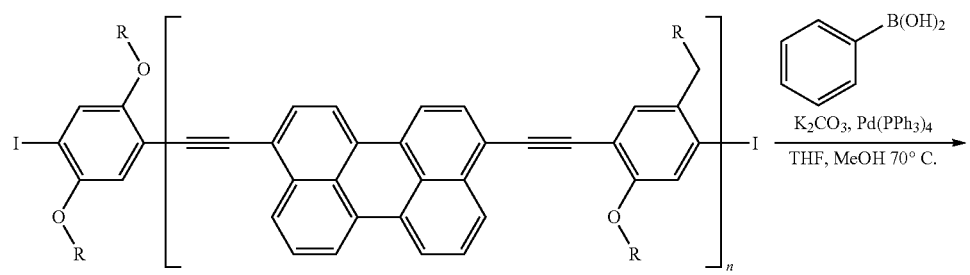

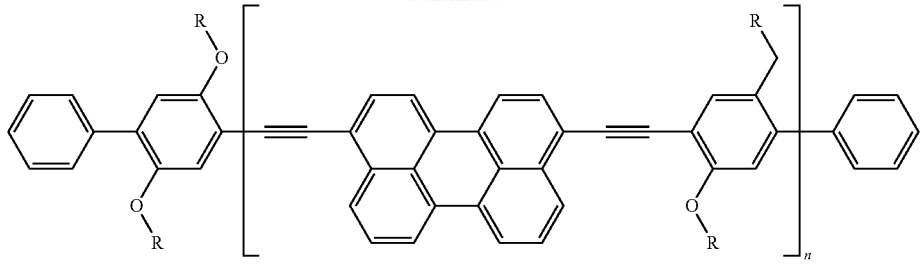

3,10-Dibromoperylene

Perylene (3.00 g, 11.9 mmol) was suspended in 130 mL of acetic acid and stirred at 40° C. A solution of bromine (1.35 mL, 26.2 mmol) in 5.0 mL of acetic acid was slowly added to the suspension of perylene at rapid stirring. The reaction mixture was stirred at 40° C. for four hours. Once cooled to room temperature the reaction was quenched with sodium thiosulfate solution, followed by addition of 300 mL of water. The product mixture was collected by filtration and dried overnight. The isomer mixture was separated by repetitive recrystallization from toluene and THF. The 3,10-dibromoperylene isomer was purified to 90% isomeric purity and taken to the next step. Orange solids. Yield: 8%. 1H NMR (400 MHz, CDCl$_3$, 25° C.): δ=8.25 (d, J=7.6 Hz, 2H), 8.12 (d, J=8.6 Hz, 2H), 7.97 (d, J=8.1 Hz, 2H), 7.77 (d, J=8.1 Hz, 2H), 7.60 (t, J=8.1 Hz, 2H) ppm.

3,10-bis(TMS-alkynyl)perylene 3,10-Dibromoperylene (90% isomer mixture) (0.310 g, 0.76 mmol) was dissolved in 20 mL of THF at 60° C. and the solution was sparged with N$_2$ for 10 minutes. Pd(PPh$_3$)$_4$ (88 mg, 0.076 mmol), and CuI (15 mg, 0.079 mmol) were added to the reaction flask against the positive flow of N$_2$ and the mixture was sparged with N$_2$ for additional 7 minutes. In another flask a solution of TMS-acetylene (0.50 mL, 3.6 mmol) in triethylamine (5 mL) was sparged with N$_2$ for 10 minutes. The solution of TMS-acetylene was added dropwise to the reaction mixture at 100° C. The reaction was stirred overnight, in the dark, under an atmosphere of N$_2$ at 60° C. The mixture was then cooled to room temperature and poured into a saturated aqueous solution of ammonium chloride; the product was extracted with dichloromethane. The combined organic layer was dried with MgSO$_4$ and the product was purified by column chromatography on silica gel using hexanes at the eluent. The product was subsequently recrystallized from dichloromethane and hexanes. Orange solids, 0.212 g Yield: 63%. 1H NMR (400 MHz, CDCl$_3$, 25° C.): δ=8.25 (d, J=7.2 Hz, 2H), 8.21 (d, J=8.5 Hz, 2H), 8.10 (d, J=7.8 Hz, 2H), 7.69 (d, J=7.8 Hz, 2H), 7.59 (t, J=8.3 Hz, 2H), 0.35 (s, 18H) ppm.

3,10-dialkynylperylene 3,10-Bis(TMS-alkynyl)perylene (195 mg, 0.438 mmol), potassium carbonate (0.975 g, 7.05 mmol), were suspended in tetrahydrofuran (40 mL) and methanol (2.5 mL) and stirred in the dark for two hours. The solvents were removed by evaporation in vacuo, and the product was purified by passing it through a silica plug using hexanes and dichloromethane (1:1) as the eluent. The solvent was removed by evaporation in vacuo and the product was used in the next step without further purification.

1,4-bis(ethyhexyoxy)benzene

Dihydroquinone (4.000 g, 36.3 mmol) and potassium carbonate (30.0 g, 217 mmol) were suspended in dimethylformamide (60 mL), and the solution was sparged with N$_2$ for 10 minutes. The reaction mixture was heated to 70° C. and 2-ethylhexylbromide (16.4 mL, 92.2 mmol) was added dropwise into a vigorously stirred reaction mixture. The reaction mixture was stirred overnight at 70° C., under an atmosphere of N$_2$. The mixture was then cooled to room temperature and 300 mL of water were added. The product was extracted with dichloromethane. The combined organic layer was dried with MgSO$_4$ and the product was purified by column chromatography on silica gel, using hexanes as the eluent. Colorless oil, 11.1 g. Yield: 91%. 1H NMR (400 MHz, CDCl$_3$, 25° C.): δ=6.82 (s, 4H), 3.78 (d, J=5.7 Hz, 4H), 1.69 (p, J=6.0 Hz, 2H), 1.55-1.24 (m, 16H), 0.94-0.87 (m, 12H) ppm.

1,4-bis(ethylhexyloxy)-2,5-diiodobenzene 1,4-Bis(ethylhexyloxy)benzene (11.0 g, 32.9 mmol), iodine (6.88 g, 54.2 mmol), periodic acid (3.44 g, 15.1 mmol), conc. sulfuric acid (4.8 mL), water (20 mL), dichloromethane (16 mL) and acetic acid (100 mL) were loaded into a round bottom flask equipped with a stir bar and a condenser. The reaction mixture was heated to 70° C. and stirred overnight. Once cooled to room temperature, the mixture was poured into a solution of sodium thiosulfate and extracted with dichloromethane. The combined organic layer was dried with MgSO$_4$ and was purified by column chromatography on silica gel using hexanes as the eluent. Colorless oil. Yield: 41%. 1H NMR (400 MHz, CDCl$_3$, 25° C.): δ=7.16 (s, 2H), 3.82 (d, J=5.4 Hz, 4H), 1.78-1.67 (m, 2H), 1.63-1.28 (m, 16H), 0.98-0.88 (m, 12H) ppm.

Oligomerization of Ethynylperylenes 1,4-bis(ethylhexyloxy)-diiodobenzene (558 mg, 0.952 mmol) was dissolved in 40 mL of tetrahydrofuran and the solution was sparged with N$_2$ for 10 minutes. Pd(PPh$_3$)$_4$ (0.114 mg, 0.0987 mmol) and CuI (0.017 mg, 0.0892 mmol) were added to the reaction flask against the flow of N$_2$, and the reaction mixture was sparged with N$_2$ for additional 7 minutes and the mixture was heated to 60° C. In another flask 3,10-dialkynylperylene (122 mg, 0.41 mmol) was dissolved in THF (12 mL) and triethylamine (12 mL) and sparged with N$_2$ for 10 minutes. The solution of 3,10-dialkynylperylene was then added dropwise to the reaction mixture and the mixture was stirred for three days, in the dark, under an atmosphere of N$_2$, at 60° C.

Terminal Phenylation of Perylene Oligomers

To the Sonogashira coupling reaction above after 3 days of heated stirring, K$_2$CO$_3$ (0.998 g, 7.22 mmol), phenylboronic acid (0.515 g, 4.22 mmol), additional Pd(PPh$_3$)$_4$ (0.095 g, 0.082 mmol) and 0.2 mL of air free methanol were added to the reaction flask against the flow of N$_2$ and the resultant reaction mixture was stirred in the dark, under an atmosphere of N$_2$ at 60° C. overnight. The mixture was then cooled to room temperature and extracted from a saturated aqueous solution of NH$_4$Cl with dichloromethane, dried with MgSO$_4$ and the solvent was removed by rotary evaporation under vacuum. The crude reaction mixture was purified by column chromatography on silica gel using hexanes and THF as the mobile phase, and the final compounds were recrystallized from THF/MeOH solvent mixture and subsequently from CH$_2$Cl$_2$/hexanes solvent mixture. Larger oligomers were produced in this reaction but could not be cleanly isolated due to their poor solubility. Yields of the small oligomers can be improved by increasing the relative concentration of the dihalide to the dialkyne in the oligomerization reaction.

NMR Data:

1-OPP Red Oil.

Yield: 1%. $^1$H NMR (400 MHz, CDCl$_3$, 25° C.): δ=8.50 (d, J=8.59 Hz, 2H), 8.31 (d, J=7.3 Hz, 2H), 8.20 (d, J=8.0 Hz, 2H), 7.79 (d, J=8.0 Hz, 2H), 7.63-7.58 (m, 6H), 7.42 (dd, J$_1$=7.3 Hz, J$_2$=8.0 Hz, 4H), 7.36-7.33 (m, 2H), 7.21 (s, 2H), 6.96 (s, 2H), 4.01 (sept, 4H), 3.86 (d, J=5.6 Hz, 2H), 1.94-1.85 (m, 2H), 1.72-1.46 (m, 12H), 1.42-1.30 (m, 22H), 0.98 (dd, J$_1$=7.5 Hz, J$_2$=8.1 Hz, 6H), 0.88-0.85 (m, 18H) ppm. $^{13}$C NMR (101 MHz, CDCl$_3$, 25° C.) δ 154.63, 150.05, 138.38, 134.69, 132.87, 132.29, 132.19, 131.42, 131.22, 130.89, 129.69, 128.44, 127.99, 127.32, 121.54, 121.14, 120.43, 117.46, 114.97, 112.24, 93.02, 92.43, 71.93, 71.87, 39.85, 39.67, 30.72, 30.65, 29.30, 29.14, 24.06, 24.04, 23.26, 23.18, 14.25, 14.23, 11.34, 11.27 ppm. HRMS (ES$^+$) (m/z), calculated for C$_{80}$H$_{92}$O$_4$ (M+H)$^+$ 1117.71, found 1117.835.

2-OPP Red Iridescent Solids.

Yield: 4%. $^1$H NMR (400 MHz, CDCl$_3$, 25° C.): δ 8.50 (J$_1$=8.5 Hz, 4H), 8.32 (d, J=7.6 Hz, 4H), 8.21 (d, J=8.2 Hz, 4H), 7.80 (d, J=7.7 Hz, 4H), 7.65-7.58 (m, 8H), 7.42 (t, J=7.4 Hz, 4H), 7.37-7.32 (m, 2H), 7.21 (s, 2H), 7.18 (s, 2H), 6.96 (s, 2H), 4.04 (m, 8H), 3.86 (d, J=5.5 Hz, 4H), 2.00-1.86 (m, 4H), 1.78-1.48 (m, 20H), 1.42-1.30 (m, 32H), 1.04-0.96 (m, 12H), 0.91-0.85 (m, 22H) ppm. $^{13}$C NMR (101 MHz, CDCl$_3$, 25° C.) δ 155.56, 154.66, 154.08, 151.66, 150.09, 138.39, 134.73, 132.96, 131.55, 131.53, 129.70, 128.58, 128.50, 128.48, 128.00, 127.11, 124.52, 123.49, 121.27, 121.24, 120.57, 115.02, 114.11, 100.10, 97.04, 91.03, 71.98, 39.87, 39.70, 31.09, 29.33, 29.16, 24.08, 23.28, 23.26, 23.19, 14.29, 14.26, 14.23, 11.37, 11.35, 11.28 ppm. HRMS (ES$^+$) (m/z), calculated for C$_{126}$H$_{138}$O$_6$ (M+H)$^+$ 1749.06, found 1749.211.

3-OPP Burgundy-Purple Solids.

Yield: 2%. $^1$H NMR (400 MHz, CDCl$_3$, 25° C.): δ=8.52-8.47 (m, 6H), 8.35-8.28 (m, 6H), 8.23-8.17 (m, 6H), 7.82-7.75 (m, 6H), 7.67-7.57 (m, 10H), 7.44-7.32 (m, 8H), 7.21 (s, 2H), 7.18 (s, 4H), 6.95 (s, 2H), 4.09-3.97 (m, 12H), 3.86 (d, J=5.6 Hz, 4H), 1.99-1.84 (m, 6H), 1.76-0.83 (m, 114H) ppm. $^{13}$C NMR (101 MHz, CDCl$_3$, 25° C.) δ 154.68, 154.06, 150.10, 138.41, 134.72, 132.96, 131.51, 131.46, 131.18, 131.09, 129.70, 128.48, 127.99, 127.40, 127.34, 127.09, 121.72, 121.41, 121.29, 121.22, 121.19, 120.53, 120.43, 117.56, 116.33, 115.03, 114.09, 112.29, 94.01, 93.15, 93.14, 93.07, 71.99, 39.88, 39.72, 30.74, 30.69, 29.34, 29.31, 29.17, 24.09, 23.29, 23.25, 23.18, 14.28, 14.23, 14.21, 11.36, 11.33, 11.27. HRMS (ES$^+$) (m/z), calculated for C$_{172}$H$_{185}$O$_8$ (M+H)$^+$ 2379.41, found 2379.623.

4-OPP Deep Purple Solids.

Yield: 5%. $^1$H NMR (400 MHz, CDCl$_3$, 25° C.): δ=8.52-8.47 (m, 8H), 8.35-8.28 (m, 8H), 8.23-8.17 (m, 8H), 7.82-7.75 (m, 8H), 7.81-7.12 (m, 26H), 6.95 (s, 1H), 6.94 (s, 1H), 4.09-3.79 (m, 20H), 1.98-0.83 (m, 150H) ppm. The compound was not sufficiently soluble to obtain good quality $^{13}$C NMR data. HRMS (ES$^+$) (m/z), calculated for C$_{218}$H$_{230}$O$_{10}$ (M+H)$^+$ 3010.76, found 3010.142.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A composition comprising:
a repeat unit defined by

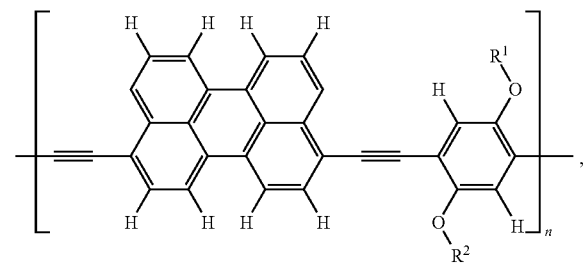

wherein:
R$^1$ and R$^2$ each comprise a hydrocarbon chain having between 1 and 10 carbon atoms, and
n is between 1 and 10, inclusively.

2. The composition of claim 1, wherein R$^1$ and R$^2$ each comprise

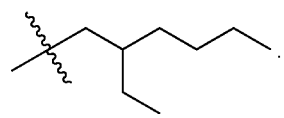 [SMILES: *CC(CC)CCCC]

3. The composition of claim 2, wherein n is between 2 and 4, inclusively.

4. The composition of claim 3, further comprising a triplet value of about 1.25 eV.

5. The composition of claim 3, further comprising a $\lambda_{max}$ value between about 538 nm and about 550 nm.

6. The composition of claim 3, further comprising a stimulated emission between about 550 nm and about 620 nm.

7. The composition of claim 3, further comprising a $E(S_1)$ value between about 2.21 eV and about 2.27 eV.

* * * * *